(12) United States Patent
Pesach et al.

(10) Patent No.: US 11,547,273 B2
(45) Date of Patent: Jan. 10, 2023

(54) USER INTERFACE FOR A DENTAL MEASUREMENT SYSTEM

(71) Applicant: Dentlytec G.P.L. LTD., Tel-Aviv (IL)

(72) Inventors: Benny Pesach, Rosh Haayin (IL); Amitai Reuvenny, Kfar-Saba (IL); Ygael Grad, Tel-Aviv (IL); Blanc Zach Lehr, Tel-Aviv (IL)

(73) Assignee: DENTLYTEC G.P.L. LTD., Tel-Aviv (IL)

( * ) Notice: Subject to any disclaimer, the term of this patent is extended or adjusted under 35 U.S.C. 154(b) by 287 days.

(21) Appl. No.: 16/648,555

(22) PCT Filed: Sep. 17, 2018

(86) PCT No.: PCT/IL2018/051058
§ 371 (c)(1),
(2) Date: Mar. 18, 2020

(87) PCT Pub. No.: WO2019/053730
PCT Pub. Date: Mar. 21, 2019

(65) Prior Publication Data
US 2020/0214538 A1 Jul. 9, 2020

Related U.S. Application Data

(60) Provisional application No. 62/559,992, filed on Sep. 18, 2017.

(51) Int. Cl.
*A61B 1/00* (2006.01)
*A61C 19/04* (2006.01)
(Continued)

(52) U.S. Cl.
CPC ............ *A61B 1/0005* (2013.01); *A61B 5/742* (2013.01); *A61C 19/04* (2013.01); *A61B 1/00009* (2013.01);
(Continued)

(58) Field of Classification Search
CPC ... A61B 5/4547; A61B 5/0064; A61B 1/0005; A61B 5/742; A61B 5/0077; A61B 1/24;
(Continued)

(56) References Cited

U.S. PATENT DOCUMENTS

2004/0218792 A1 11/2004 Spoonhower et al.
2005/0237581 A1 10/2005 Knighton et al.
(Continued)

FOREIGN PATENT DOCUMENTS

CN 201537079 U 8/2010
CN 105125159 A 12/2015
(Continued)

OTHER PUBLICATIONS

Supplementary European Search Report and the European Search Opinion dated Apr. 30, 2021 From the European Patent Office Re. Application No. 18857091.5. (9 Pages).
(Continued)

*Primary Examiner* — Brenda C Bernardi
(74) *Attorney, Agent, or Firm* — Cooley LLP

(57) ABSTRACT

Some of the embodiments of the present disclosure are directed to a dental measurement method comprising: measuring an orientation of a dental measurement device includes a user interface; and displaying information on said user interface based on said orientation.

20 Claims, 21 Drawing Sheets

(51) Int. Cl.
  *A61B 5/00*   (2006.01)
  *A61B 1/04*   (2006.01)
  *A61B 1/24*   (2006.01)
  *A61C 9/00*   (2006.01)
  *A61B 5/06*   (2006.01)

(52) U.S. Cl.
  CPC . *A61B 1/04* (2013.01); *A61B 1/24* (2013.01); *A61B 5/0088* (2013.01); *A61B 5/064* (2013.01); *A61B 5/067* (2013.01); *A61B 5/6885* (2013.01); *A61C 9/0053* (2013.01)

(58) Field of Classification Search
  CPC ..... A61B 1/00009; A61B 1/04; A61B 5/0088; A61B 5/067; A61B 5/064; A61B 5/6885; A61B 1/00043; A61C 19/04; A61C 9/0053
  See application file for complete search history.

(56) References Cited

U.S. PATENT DOCUMENTS

| | | |
|---|---|---|
| 2008/0038688 A1 | 2/2008 | Kopelman et al. |
| 2010/0189341 A1 | 7/2010 | Oota et al. |
| 2013/0257718 A1 | 10/2013 | Öjelund et al. |
| 2015/0348320 A1 | 12/2015 | Pesach et al. |
| 2016/0259515 A1 | 9/2016 | Sabina et al. |
| 2016/0338803 A1 | 11/2016 | Pesach |
| 2020/0060550 A1* | 2/2020 | Pesach ............... A61B 1/00009 |
| 2020/0121429 A1* | 4/2020 | Pesach ................ A61C 9/0053 |

FOREIGN PATENT DOCUMENTS

| | | |
|---|---|---|
| WO | WO 2011/011193 A1 | 1/2011 |
| WO | WO 2017/125926 A2 | 7/2017 |
| WO | WO 2019/053730 A1 | 3/2019 |

OTHER PUBLICATIONS

International Preliminary Report on Patentability dated Apr. 2, 2020 From the International Bureau of WIPO Re. Application No. PCT/IL2018/051058. (10 Pages).
International Search Report and the Written Opinion dated Jan. 3, 2019 From the International Searching Authority Re. Application No. PCT/IL2018/051058. (19 Pages).

* cited by examiner

USER INTERFACE FOR A DENTAL MEASUREMENT SYSTEM

RELATED APPLICATIONS

This Application is a National Phase of PCT Patent Application No. PCT/IL2018/051058 having International filing date of Sep. 17, 2018, which claims the benefit of priority under 35 USC § 119(e) of U.S. Provisional Patent Application No. 62/559,992 filed on Sep. 18, 2017. The contents of the above applications are all incorporated by reference as if fully set forth herein in their entirety.

FIELD AND BACKGROUND OF THE DISCLOSURE

The present disclosure, in some embodiments thereof, relates to user interfaces for a dental measurement system and, more particularly, but not exclusively, to user interfaces for a dental measurement device.

SUMMARY OF SOME OF THE EMBODIMENTS OF THE DISCLOSURE

According to an aspect of some embodiments of the present disclosure there is provided a dental measurement control method for controlling a dental measurement system which comprises measuring movement of a dental tool, and controlling the system using measured movement of the dental measurement device.

According to some embodiments of the disclosure, the dental tool is a dental measurement device.

According to some embodiments of the disclosure, movement comprises one or more of translation of the dental measurement device in space and change in orientation of the dental measurement device.

According to some embodiments of the disclosure, the system comprises a display and controlling comprises controlling a selected portion of the display based on the measured movement.

According to some embodiments of the disclosure, the system comprises a display, and controlling comprises controlling a position of a cursor on the display based on the measured movement.

According to some embodiments of the disclosure, measuring comprises movement with respect to at least a portion of a patient's mouth.

According to some embodiments of the disclosure, the system comprises a display, and a 3D model is displayed on the display.

According to some embodiments of the disclosure, controlling comprises controlling an orientation of a 3D model displayed on the display based on the measured movement.

According to some embodiments of the disclosure, measuring comprises registering a dental measurement device coordinate space with a 3D model coordinate space. Controlling comprises controlling the display of the 3D model using the measured movement of the dental measurement device within the dental measurement device coordinate space, or measuring comprises registering a dental measurement device coordinate space and a patient mouth portion coordinate space with a 3D model coordinate space.

In some such embodiments, the controlling comprises controlling the display of the 3D model using the measured movement of the dental measurement device with respect to the patient mouth portion.

According to some embodiments of the disclosure, registering comprises registering using one or more marker.

According to some embodiments of the disclosure, the one or more marker includes at least one marker within a patient's mouth.

According to some embodiments of the disclosure, the method comprises comprising marking the 3D model with a position of a measured contact between a dental measurement device stylus and a portion of a patient's mouth.

According to some embodiments of the disclosure, the method comprises displaying the marked 3D model.

According to some embodiments of the disclosure, the method comprises collecting measurements of at least a portion of a patient's mouth using the dental measurement device; and generating a 3D model based on the measurements.

According to some embodiments of the disclosure, the 3D model comprises one or more of CT data, MRI data and ultrasound data.

According to some embodiments of the disclosure, the measuring comprises measuring contact of a stylus of the dental measurement device.

According to some embodiments of the disclosure, the measuring comprises identifying contact between the dental measurement device stylus and a portion of a patient's mouth.

According to some embodiments of the disclosure, the measuring comprises measuring using images collected by an imager of the dental measurement device.

According to some embodiments of the disclosure, the dental measurement device comprises an imager and circuitry configured to generate a model of at least a portion of a mouth from images acquired by the imager.

According to an aspect of some embodiments of the present disclosure there is provided a dental measurement method comprising inserting at least a portion of a dental measurement device including a final optical element of an imager into a patient's mouth, and collecting images with the dental measurement device imager the images including one or more of: a portion of the dental measurement device obscured from a user's line of sight, and a portion of the patient's mouth obscured from a user's line of sight. Such embodiments may also include displaying the images.

According to some embodiments of the disclosure, the displaying comprises displaying the images on one or more display mounted on the dental measurement device.

According to some embodiments of the disclosure, the method comprises identifying, portions of the images including one or more view obscured from a user's line of sight; and displaying the one or more view.

According to some embodiments of the disclosure, identifying comprises, identifying, from the images, a portion of the images obscured from a user's line of sight which, when displayed on the display align with a user view of patient mouth portions. Displaying comprises displaying the portion of the images.

According to an aspect of some embodiments of the present disclosure there is provided a dental measurement system comprising an intraoral scanner (IOS) comprising an imager, and a distal portion sized and shaped for insertion into a human mouth comprising a final optical element of the imager, at least one display configured to display images collected by the imager.

According to some embodiments of the disclosure, the system comprises circuitry configured to generate a model of at least a portion of a mouth from images acquired by the imager.

According to some embodiments of the disclosure, the system comprises a light configured to illuminate at least a portion of the human mouth with structured light.

According to some embodiments of the disclosure, the system comprises a light configured to illuminate at least a portion of the human mouth with structured light; and circuitry configured to generate a model of the at least a portion of the human mouth from images acquired by the imager.

According to some embodiments of the disclosure, the dental measurement device includes a stylus.

According to some embodiments of the disclosure, the stylus is sized and shaped for insertion between a tooth and surrounding gingiva.

According to some embodiments of the disclosure, the display is orientated at 30-90° from a central long axis of the stylus. According to some embodiments of the disclosure, the display is orientated at 0-60° from a central long axis of the stylus. According to some embodiments of the disclosure, the display is mounted on the distal portion. According to some embodiments of the disclosure, the display is disposed on a top side of the dental measurement device. According to some embodiments of the disclosure, the display is orientated at 30-90° from a central axis of a field of view of the imager. According to some embodiments of the disclosure, the display is disposed on a lateral side of the dental measurement device. According to some embodiments of the disclosure, the display is orientated at 0-60° from a central axis of a field of view of the imager.

According to some embodiments of the disclosure, the system comprises circuitry configured to process images collected by the imager. The display is configured to display processed images.

According to some embodiments of the disclosure, the dental measurement device includes a plurality of displays. According to some embodiments of the disclosure, the system comprises one or more sensors configured to sense an orientation of the dental measurement device and circuitry for selecting, based on the orientation, one or more display from the plurality of displays for display of information.

According to some embodiments of the disclosure, the system comprises one or more sensors configured to sense an orientation of the dental measurement device, and circuitry for orientating display of the images on the at least one display based on the orientation.

According to some embodiments of the disclosure, the display is disposed on more than one lateral side of the dental measurement device, extending from a first lateral side to one or more lateral sides of the intraoral scanner. According to some embodiments of the disclosure, the display is a flexible display, where the flexible display may be wrapped around a portion of the intraoral scanner.

According to an aspect of some embodiments of the present disclosure there is provided a dental measurement method comprising measuring an orientation a dental measurement device, and displaying information on a user interface mounted on the dental measurement device, based on the orientation.

According to some embodiments of the disclosure, measuring comprises measuring an orientation of a portion of the dental measurement device including the user interface.

According to some embodiments of the disclosure, the information includes:
images collected by an imager of the dental measurement device;

processed images collected by and imager of the dental measurement device; and/or
feedback regarding measurements collected using the dental measurement device.

According to some embodiments of the disclosure, measuring comprises:
measuring the orientation of the dental measurement device with respect to gravity;
measuring with one of more gyroscope; and/or
measuring the orientation of the dental measurement device with respect to a dental object.

According to some embodiments of the disclosure, the dental object is a tooth.

According to some embodiments of the disclosure, the method comprises identifying the dental object and an orientation of the dental measurement device with respect to the dental object, from images collected by an imager of the dental measurement device.

According to some embodiments of the disclosure, the measuring comprises:
measuring the orientation of the dental measurement device with respect to a user;
measuring orientation using one of more position sensor; and/or
measuring orientation using images collected by one or more imager.

According to some embodiments of the disclosure, the one or more imager comprises an imager of the dental measurement device.

According to an aspect of some embodiments of the present disclosure there is provided a dental measurement system comprising a dental tool comprising a distal portion sized and shaped for insertion into a human mouth circuitry configured to generate a signal based on movement of the dental measurement device, and control one or more aspect of the system based on the signal.

According to some embodiments of the disclosure the tool is a dental measurement device comprising an imager and the distal portion comprises a final optical element of the imager.

According to some embodiments of the disclosure the dental measurement device includes at least one position sensor configured to generate the signal.

According to some embodiments of the disclosure the position sensor is an inertial measurement unit configured to produce a signal based on an orientation of the dental measurement device.

According to some embodiments of the disclosure the circuitry generates the signal using images collected by the imager.

According to some embodiments of the disclosure the one or more aspect includes selection of a portion of the display.

According to some embodiments of the disclosure the one or more aspect includes position of a cursor on the display.

According to some embodiments of the disclosure the dental measurement device includes one or more user interface configured to generate a second signal, and the circuitry is configured to control selection of a portion of the display based on the signal and the second signal.

According to some embodiments of the disclosure the one or more aspect includes orientation of display of a 3D model on the display.

According to an aspect of some embodiments of the present disclosure there is provided a dental measurement control method for control of a dental measurement system and comprises measuring a gesture performed with a dental tool using one or more sensor to produce a measurement signal, identifying a user command from the measurement signal, generating a control signal based on the identified user command, and modifying function of one or more system component based on the control signal.

According to some embodiments of the disclosure, the dental tool is a dental measurement device.

According to some embodiments of the disclosure:

the gesture comprises moving the dental measurement device, the gesture comprises translating the dental measurement in space, the gesture comprises changing an orientation of the dental measurement device, the gesture comprises contacting a portion of the dental measurement device to an object, and/or the gesture comprises changing a proximity of the dental measurement device to an object.

According to some embodiments of the disclosure the object is a portion of a patient's mouth. According to some embodiments of the disclosure, the object is a second dental device, According to some embodiments of the disclosure:

modifying comprises initiating a start to collection of measurements with the dental measurement device;

modifying comprises activating a second dental device;

modifying comprises collecting a color measurement; and/or modifying comprises collecting a snapshot image.

According to some embodiments of the disclosure, a method is provided and comprises inputting a command through a user interface to produce a user interface signal, and identifying a user command from the measurement signal and the user interface signal.

According to an aspect of some embodiments of the present disclosure there is provided a dental measurement method comprising:

measuring an orientation of a dental measurement device comprising a user interface; and displaying information on the user interface, based on the orientation.

According to some embodiments of the disclosure the measuring comprises measuring the orientation of the dental measurement device with respect to a dental object.

According to some embodiments of the disclosure the measuring comprises measuring an orientation of a portion of the dental measurement device including the user interface.

According to some embodiments of the disclosure the information includes feedback regarding measurements collected using the dental measurement device.

According to some embodiments of the disclosure the information includes feedback regarding measurements collected using the dental measurement device, and the feedback is based on the orientation of the dental measurement device with respect to the dental object.

According to some embodiments of the disclosure the feedback is one or more of visual, audio, and haptic feedback.

According to some embodiments of the disclosure the feedback is related to an angle between the dental measurement device and the dental object.

According to some embodiments of the disclosure the measuring comprises: illuminating the dental object with structured light; and collecting images of the illuminated dental object; wherein the feedback indicates whether the angle is above a threshold associated with distortion of the structured light.

According to some embodiments of the disclosure the dental measurement device includes a stylus; wherein the measuring comprises contacting the stylus to the dental object;

wherein the feedback is related to one or more of: an angle of the stylus with respect to the dental object; and a force of contact of the stylus with the dental object.

According to some embodiments of the disclosure wherein the dental measurement device includes a stylus; wherein the measuring comprises measuring deflection of the stylus; wherein the feedback is related to the deflection of the stylus.

According to some embodiments of the disclosure the dental object is at least a portion of a tooth.

According to some embodiments of the disclosure the measuring comprises identifying, from images collected by an imager of the dental measurement device, one or more of: the dental object; and an orientation of the dental measurement device with respect to the dental object.

According to some embodiments of the disclosure the measuring comprises measuring the orientation of the dental measurement device with respect to gravity.

According to some embodiments of the disclosure the measuring comprises measuring orientation using images collected by one or more imager.

According to some embodiments of the disclosure the measuring comprises measuring the orientation of the dental measurement device with respect to a position of a user and with respect to the dental measurement device.

According to some embodiments of the disclosure the measuring comprises identifying the position of the user with respect to the dental measurement device, from images collected by an imager of the dental measurement device.

According to some embodiments of the disclosure the dental measurement device includes a plurality of user interfaces; the method comprising selecting one or more user interface from the plurality of user interfaces, based on the orientation.

According to some embodiments of the disclosure the measuring comprises: inserting at least a portion of the dental measurement device, which portion including a final optical element of an imager into a patient's mouth; collecting an image with the dental measurement device imager the image including one or more of: a portion of the dental measurement device obscured from a user's line of sight; and a portion of the patient's mouth obscured from a user's line of sight; and displaying the image.

According to some embodiments of the disclosure the method comprises identifying one or more portion of the image including one or more view obscured from a user's line of sight, and displaying the one or more view.

According to some embodiments of the disclosure the displaying comprises displaying the image on one or more display of the dental measurement device.

According to some embodiments of the disclosure the method comprises identifying, from the image, a portion of the image obscured from a user's line of sight which, when displayed on the display aligns with a user view of patient mouth portions, and displaying comprises displaying the portion of the image.

According to some embodiments of the disclosure said identifying comprises identifying said user's line of sight, using one or more image of said user captured using one or more imager of said dental measurement device.

According to an aspect of some embodiments of the present disclosure there is provided a dental measurement system comprising:

an intraoral scanner (IOS) comprising:

an imager;

a distal portion sized and shaped for insertion into a human mouth comprising a final optical element of the imager; and at least one display configured to display images collected by the imager.

According to some embodiments of the disclosure the display is disposed on the distal portion.

According to some embodiments of the disclosure the system comprises one or more sensor configured to sense an orientation of said dental measurement device.

According to some embodiments of the disclosure the system comprises circuitry for orientating display of the images on the at least one display, based on the orientation.

According to some embodiments of the disclosure the dental measurement device includes a plurality of displays; the system comprising circuitry for selecting, based on the orientation, one or more display from the plurality of displays for display of the images.

According to some embodiments of the disclosure the dental measurement device includes a stylus.

According to some embodiments of the disclosure the system comprises circuitry configured to process images collected by the imager, wherein the at least one display is configured to display processed images.

According to some embodiments of the disclosure the at least one display is disposed on more than one lateral side of the dental measurement device, extending from a first lateral side to one or more lateral sides of the intraoral scanner.

According to some embodiments of the disclosure the at least one display is a flexible display.

According to some embodiments of the disclosure the flexible display is wrapped around a portion of the intraoral scanner.

According to some embodiments of the disclosure the system comprises circuitry for selecting, based on the orientation, one or more portion of the display for display of the images.

According to an aspect of some embodiments of the present disclosure there is provided a method of control of a dental measurement system comprising: measuring one or more of: movement of a stylus of a dental measurement device; and contact between the stylus and an object; controlling the system using the measuring.

According to some embodiments of the disclosure the measuring the movement of the stylus comprises measuring movement with respect to one or more of: a portion of a patient's mouth; a portion of a user's body; and a dental tool.

According to some embodiments of the disclosure the movement of the stylus comprises one or more of translation of the stylus in space and change in orientation of the stylus.

According to some embodiments of the disclosure the measuring comprises measuring using images collected by one or more imager of the dental measurement device.

According to an aspect of some embodiments of the present disclosure there is provided a dental measurement control method for control of a dental measurement system which comprises: measuring a gesture performed with a dental measurement device using one or more sensor to produce a measurement signal; identifying a user command from the measurement signal; generating a control signal based on the identified user command; and modifying function of one or more component of the dental measurement device based on the control signal.

According to some embodiments of the disclosure the gesture comprises one or more of: moving the dental measurement device; translating the dental measurement device in space; changing an orientation of the dental measurement device with respect to an object; contacting a portion of the dental measurement device to an object; and changing a proximity of the dental measurement device to an object.

According to some embodiments of the disclosure the object is a portion of a patient's mouth.

According to some embodiments of the disclosure the object is a second dental device.

According to some embodiments of the disclosure the modifying comprises initiating a start to collection of measurements with the dental measurement device. According to some embodiments of the disclosure the modifying comprises modifying function of a second dental device.

According to some embodiments of the disclosure the modifying comprises collecting a color measurement. According to some embodiments of the disclosure the modifying comprises collecting a snapshot image.

According to an aspect of some embodiments of the present disclosure there is provided a method of control of a dental measurement system comprising:

receiving a 3D model of at least a portion of a patient's mouth;

registering dental measurement device coordinate space and a patient mouth portion coordinate space with a 3D model coordinate space of the 3D model;

measuring movement of the dental measurement device with respect to the patient mouth portion;

controlling a display of the 3D model using the measured movement of the dental measurement device with respect to the patient mouth portion.

According to some embodiments of the disclosure the registering comprises registering using one or more marker. According to some embodiments of the disclosure the one or more marker includes at least one marker within a patient's mouth.

According to some embodiments of the disclosure the method comprises marking the 3D model with a position of measured contact between a dental measurement device stylus and a portion of a patient's mouth.

According to some embodiments of the disclosure the method displaying the marked 3D model.

According to some embodiments of the disclosure the receiving comprises: collecting measurements of at least a portion of a patient's mouth using the dental measurement device; and generating the 3D model based on the measurements.

According to some embodiments of the disclosure the dental measurement device comprises at least one imager; wherein the receiving comprises and comprises generating the 3D model a mouth from images acquired by the at least one imager.

According to some embodiments of the disclosure the receiving comprises receiving a 3D model including one or more of CT data, MRI data and ultrasound data.

Unless otherwise defined, all technical and/or scientific terms used herein have the same meaning as commonly understood by one of ordinary skill in the art to which the disclosure pertains. Although methods and materials similar or equivalent to those described herein can be used in the practice or testing of embodiments of the disclosure, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the disclosure can involve performing or completing selected tasks manually, automatically, or a combination thereof. Moreover, according to actual instrumentation and equipment of embodiments of the method and/or system of the disclosure, several selected tasks could be implemented by hardware, by software or by firmware or by a combination thereof using an operating system.

For example, hardware for performing selected tasks according to embodiments of the disclosure could be implemented as a chip or a circuit. As software, selected tasks according to embodiments of the disclosure could be implemented as a plurality of software instructions being executed by a computer using any suitable operating system. In an exemplary embodiment of the disclosure, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

As will be appreciated by one skilled in the art, aspects of the present disclosure may be embodied as a system, method or computer program product. Accordingly, aspects of the present disclosure may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, some embodiments of the present disclosure may take the form of a computer program product embodied in one or more computer readable medium(s) having computer readable program code embodied thereon. Implementation of the method and/or system of some embodiments of the disclosure can involve performing and/or completing selected tasks manually, automatically, or a combination thereof. Moreover, according to actual instrumentation and equipment of some embodiments of methods, systems, and/or computer program products of the present disclosure, several selected tasks could be implemented by hardware, by software or by firmware and/or by a combination thereof, e.g., using an operating system.

For example, hardware for performing selected tasks according to some embodiments of the present disclosure could be implemented as a chip or a circuit. As software, selected tasks according to some embodiments of the present disclosure could be implemented as a plurality of software instructions being executed by a computer using any suitable operating system. In an exemplary embodiment, one or more tasks according to some exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

Any combination of one or more computer readable medium(s) may be utilized for some embodiments. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium and/or data used thereby may be transmitted using any appropriate medium, including but not limited to wireless, wireline, optical fiber cable, RF, etc., or any suitable combination of the foregoing.

Computer program code for carrying out operations for some embodiments of the present disclosure may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Some embodiments of the present disclosure may be described below with reference to flowchart illustrations and/or block diagrams of methods, apparatus (systems) and computer program products. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

BRIEF DESCRIPTION OF THE SEVERAL VIEWS OF THE DRAWINGS

Some embodiments of the disclosure are herein described, by way of example only, with reference to the accompanying drawings. With specific reference now to the drawings in detail, it is stressed that the particulars shown are by way of example and for purposes of illustrative discussion of embodiments of the disclosure. In this regard, the description taken with the drawings makes apparent to those skilled in the art how embodiments of the disclosure may be practiced.

In the drawings.

DESCRIPTION OF SOME EMBODIMENTS OF THE DISCLOSURE

Figure 1:
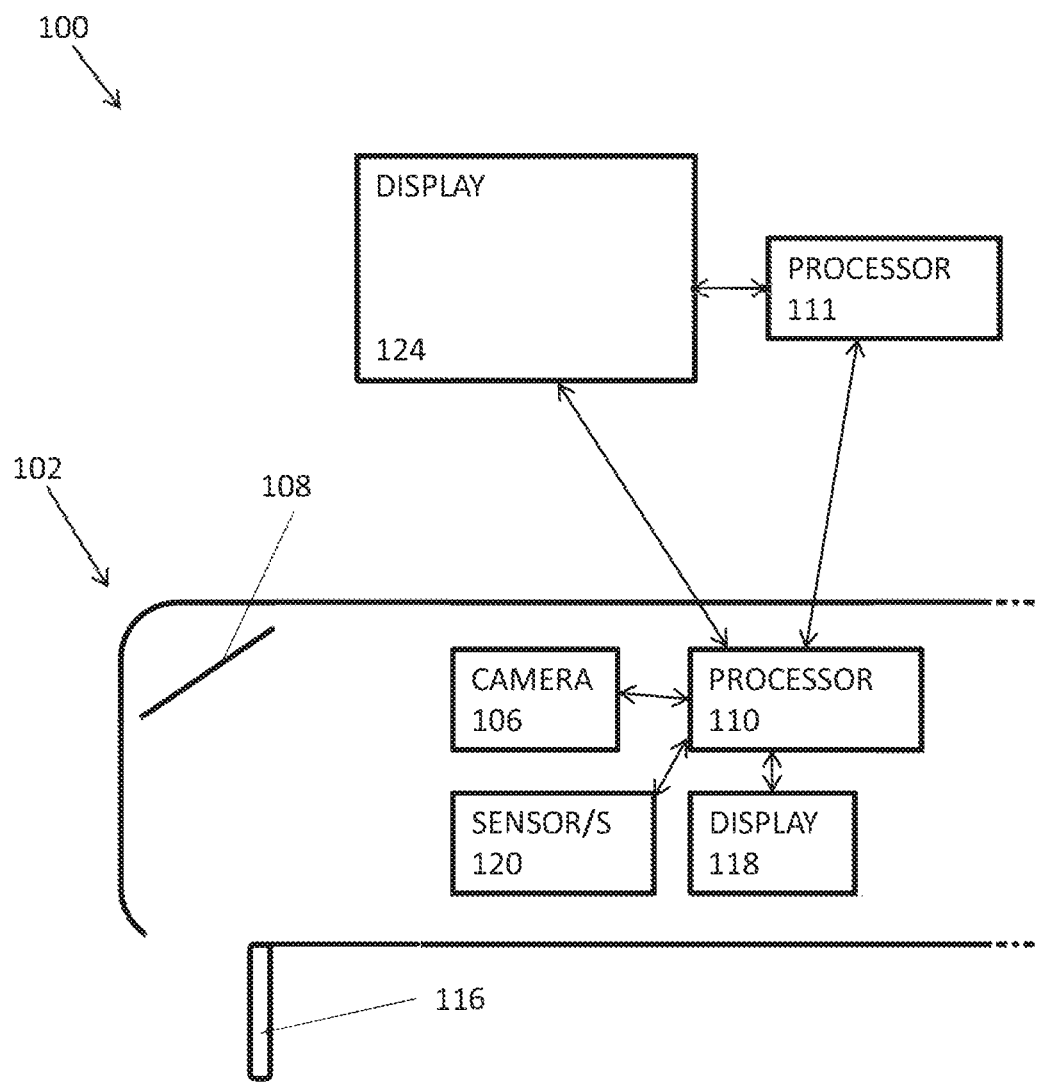
FIG. 1 is a simplified schematic of an exemplary dental measurement system according to some embodiments of the disclosure.

The present disclosure, in some embodiments thereof, relates to user interfaces for a dental measurement system and, more particularly, but not exclusively, to user interfaces for a dental measurement device.

A broad aspect of some embodiments of the disclosure relates to displaying information on or by a dental measurement device, where the information aids collection of dental measurements with the dental measurement device.

An aspect of some embodiments of the disclosure relates to a dental measurement device including an imager configured to collect dental measurements and at least one user interface (e.g. visual user interface e.g. display) forming part of and/or mounted on the dental measurement device (e.g. mounted on a body of the dental measurement device). In some embodiments, the dental measurement device includes one or more audio and/or haptic user interface. In some embodiments, the dental measurement device is part of a dental measurement system, the system, in some embodiments including circuitry configured to generate a model of a mouth portion using measurement data collected by the imager. In some embodiments, one or more dental measurement device display is located on a portion of the dental measurement device sized and/or shaped for insertion into a patient's mouth. In some embodiments, the dental measurement device is an intraoral scanner (IOS). In some embodiments, display/s on the dental measurement device display images (optionally processed images) collected by the imager.

A potential advantage of display of information on the dental measurement device is user ability to view the dental measurement device and/or patient's mouth and the displayed information in a same region of space and/or without turning of the user's head, for example, potentially enabling the user to collect measurement data while viewing the information.

In some embodiments, the dental measurement device includes an elongate element (e.g. a stylus) sized and/or shaped to be inserted sub-gingivally (e.g. between a tooth surface and gingiva, e.g. without damaging the gingiva). In some embodiments, display includes information as to position of the stylus (e.g. image/s including at least a portion of the stylus, for example, the display potentially enabling a user to accurately control position of the stylus (e.g. with respect to a tooth and/or surrounding tissue). In some embodiments, at least a portion of the stylus is within a field of view (FOV) of the imager.

A broad aspect of some embodiments of the disclosure relates to display of information on a dental measurement device where user interface/s (e.g. display/s) and/or information displayed is responsive to an orientation of the dental measurement device. In some embodiments, an orientation of the dental measurement device changes as measurements are collected. For example, as the measurement device scans (e.g. is scanned around) a dental object (e.g. tooth) being measured.

In some embodiments, an orientation of information displayed is based on a measured orientation of the dental measurement device.

In some embodiments, an orientation of information displayed is based on a measured orientation of the dental measurement device with respect to a user's line of sight.

In some embodiments, a user's line of sight is estimated from images collected using one or more camera on the dental measurement device and/or external to the measurement device (e.g. on a system display and/or mounted in a dental clinic room). In some embodiments, user facial feature/s (e.g. eye position) are extracted from collected images to provide an estimation of user line of sight.

In some embodiments, one or more user interface (e.g. display e.g. speaker e.g. haptic feedback actuator) is activated and/or deactivated and/or selected based on an orientation of the dental measurement device e.g. with respect to a user's line of sight. For example, in some embodiments, when a top surface of the measurement device is in a line of sight of a user a display on the top surface is selected and/or activated. In some embodiments, if the measurement device is reoriented such that a side surface of the measurement device is in a line of sight of a user and/or the top surface is obscured, a display on the side surface is selected and/or activated.

In some embodiments, e.g. when a display is partially visible to a user, display of information on a user interface depends on a visible portion of the display. For example, in some embodiments, images displayed are processed (e.g. cropped and/or sized) before display on the partially visible display.

An aspect of some embodiments of the disclosure relates to displaying information regarding measurement of a dental object is (e.g. on the dental measurement device), where the displayed feedback information maintains an orientation with respect to the dental object. For example, where orientation of the feedback is maintained when an orientation of the dental measurement device is changed, e.g. during collection of measurements.

In some embodiments, displayed information (displayed visually and/or audibly and/or haptically) includes feedback as to whether enough measurement data has been collected, e.g. for region/s of the dental object, e.g. enough measurement data for construction of a prosthetic. In some embodiments, feedback provides information as to an angle between a dental measurement device stylus and a surface of a dental object (e.g. a side wall of a tooth) which is being measured.

An aspect of some embodiments of the disclosure relates to display of images of obscured views. For example, where a portion of the patient's mouth being measured and/or a portion of the dental measurement device is obscured by one or more of the dental device itself, mouth portion/s, other dental devices (e.g. within the mouth) and portion/s of the user (e.g. a user hand). In some embodiments, images collected by the dental measurement device, e.g. of obscured view/s, are displayed to a user. In some embodiments, images collected are processed to identify obscured views from collected images which are then displayed. In some embodiments, spatial position of user eyes and/or the dental measurement device and/or the mouth portion/s being measured are used to identify obscured views. For example, in some embodiments, position of the dental measurement device and/or user eye/s are located within a coordinate system of a 3D model of a mouth portion (e.g. generated from measurements collected by the dental measurement device), e.g. using collected images and/or known and/or estimated dimensions.

In some embodiments, an obscured portion of a patient's mouth is displayed, where, for example, the portion is obscured by the measurement device. In some embodiments, display of the obscured portion is on a dental measurement device display. In some embodiments, image/s displayed on the measurement device are aligned with visible mouth portions. Where, for example, image/s collected by the dental measurement device are processed before display so that the displayed images align with visible mouth portions. For example, in some embodiments, identified location/s of the dental measurement device with respect to the user's line of sight and/or the mouth portion being measured are used to display an image of the mouth portion on a display at a same location in the user field of view as the mouth portion would appear if the dental measurement device was not blocking the line of sight to the mouth portion.

A broad aspect of some embodiments of the disclosure relates to controlling a dental system including a dental measurement device, using the dental measurement device.

For example, in some embodiments, a system includes a dental measurement device and a user interface. For example, in some embodiments, movement and/or position and/or orientation of the dental measurement device (which, in some embodiments, is an IOS) controls one or more aspect of operation of a dental measurement system. In some embodiments, the dental measurement device includes a stylus and measured movement and/or position and/or orientation of the stylus controls one or more aspect of operation of a dental measurement system.

A potential advantage being preservation of sterility, for example, compared with controlling system aspect/s using a non-sterile user input device (e.g. non-sterile mouse, screen, control console). A further potential advantage is ease of control of the system, where a user holding the dental measurement device for collection of measurements is also able to control system aspect/s using the dental measurement device (e.g. the user does not need to pick up another device and/or put down the dental measurement device).

In some embodiments, measured movement and/or orientation and/or position of the dental measurement device (e.g. of the stylus) controls a display. In an exemplary embodiment, measured orientation of a dental measurement device provides a control signal, where, orientation is, for example, measured by an inertial measurement unit (IMU).

In some embodiments, the measurements control selection of a portion of a display and/or a location of a cursor on a display.

In some embodiments, the dental measurement device includes one or more user interface, for example, one or more button and/or rotation wheel. Where, in some embodiments, user interface/s are used to select a cursor location and/or confirm a selected display portion and/or where a rotation wheel is used to scroll information on a display.

In some embodiments, movement and/or orientation and/or position of the dental measurement device (e.g. the stylus) controls orientation of a displayed 3D model e.g. a model of a patient mouth portion.

In some embodiments, real space position of the measurement device and/or mouth portion/s are aligned with the model. Then, for example, in some embodiments, movement of the measurement device (e.g. stylus) with respect to the user's mouth is used to control orientation of display of the model and/or is used to add information to the model.

For example, in some embodiments, a user selects (e.g. zooms in on) a portion of the displayed model by pointing the stylus at and/or moving the stylus towards a corresponding portion of the patient's mouth (and/or of a physical model of the patient's mouth e.g. dental impression and/or cast).

For example, in some embodiments, a stylus of the measurement device is contacted to mouth portions to add information to a mouth model (e.g. marking the mouth model e.g. marking a finish line of a prepared tooth). In some embodiments, the model is generated based on previously collected measurements with the dental measurement device. Alternatively, or additionally, in some embodiments, the model is generated using CT and/or MRI and/or ultrasound data.

An aspect of some embodiments of the disclosure relates to a user controlling a dental measurement system including a dental measurement device by performing gesture/s with the dental measurement device. In some embodiments, the system recognizes gestures of different types.

For example, contact gestures, including contacting a portion (e.g. as stylus) of the dental measurement device to another object.

For example, movement and/or orientation gestures, of the dental measurement device e.g. of the stylus of the measurement device, e.g. with respect to another object, for example, a dental object (e.g. tooth) and/or a dental tool and/or a portion of a user.

For example, vocal commands.

For example, user body movement gestures, for example, facial movement/s e.g. eye movement/s, blinking, mouth movements (e.g. open, close, smile). For example user arm and/or hand movements. Where the user body movements are, in some embodiments, measured using images which, in some embodiments, include images collected by one or more imager of the dental measurement device. In some embodiments, user body movement gestures are measured with respect to the dental measurement device and/or another object. For example, in some embodiments, a user looks at a portion of the dental measurement device to modify the function of the portion (e.g. to select and/or activate, and/or modify function of the portion).

In some embodiments, a user looks at a dental object and/or a portion of a patient's mouth to control the dental measurement device, for example, to direct one or more function of the dental measurement device towards the object and/or portion. For example, in some embodiments, a user looks at a portion of a patient's mouth to one or more of; illuminate the portion with one or more light projector of the dental measurement device, initiate and/or direct measurements towards the portion, select one or more user interface, based on an estimated line of sight of the user with respect to the portion. In some embodiments, the line of sight of the user with respect to the portion of a patient's mouth is estimated using sensor data, for example, images collected by one or more imager e.g. one or more imager of the dental measurement device. In some embodiments, estimated user line of sight is used to control one or more additional dental tool.

In some embodiments, a control gesture includes more than one type of input gesture, for example, a control gesture including both contact and movement.

In some embodiments, gestures are identified by the system (e.g. by a processor receiving signal/s from sensor/s) the gesture/s then controlling aspects of the system. For example, one or more of, a start and stop to measurements, a mode of operation of the system. Where exemplary modes of operation include, for example, a display mode where the device is used to control a display, a measurement mode where the device collects dental measurements, a color measurement mode where the device collects color measurement/s, a snapshot mode where a still image is collected and/or displayed by the dental measurement device (e.g. upon a gesture and/or user input at a user interface). For example, in an exemplary embodiment, a user taps a tooth portion with the stylus to initiate a start to measurements with the dental measurement device.

In portion/s of this document the terms "dental measurement device", "measurement device" and "device" are interchangeably used.

In some embodiments the dental measurement device is:
an intraoral camera;
an intraoral camera including an IMU;
an intraoral camera including a stylus;
a dental microscope; and/or
a dental microscope, where a dental measurement device display is viewed through a microscope eyepiece.

In some embodiments, the described user interface is used not only for dental measurement devices, but also for broad range of dental tools. For example, in some embodiments, the tool is a dental drill where described user interface features are used to control parameters such as drill speed, turning on and/or off a water stream, flow rate, drill sound level and/or tone. Exemplary tools include suction device, dental laser, airotor, dental ultraviolet and/or other light source (e.g. for curing).

In some embodiments, a dental measurement device displays (e.g. on a portion of the device sized and/or shaped for insertion into a mouth) one or more color.

In some embodiments, a comparison is made (e.g. by a user) between the displayed color with colors of tissue within a patient's mouth. In some embodiments, e.g. after performing the comparison, a user selects one or more color, e.g. based on the comparison. For example, in some embodiments, a user selects a color for a dental prosthetic by comparing color/s displayed on the dental measurement device with color/s of a tooth or teeth in the patent's mouth. In some embodiments, the color/s displayed on the dental measurement device are displayed by an electronic display (e.g. screen). Alternatively or additionally, in some embodiments, the dental measurement device includes one or more colored portion of an outer surface of the dental measurement device.

Before explaining at least one embodiment of the disclosure in detail, it is to be understood that the disclosure is not necessarily limited in its application to the details of construction and the arrangement of the components and/or methods set forth in the following description and/or illustrated in the drawings and/or the Examples. The disclosure is capable of other embodiments or of being practiced or carried out in various ways.

Exemplary System According to Some Embodiments

FIG. 1 is a simplified schematic of an exemplary dental measurement system 100, according to some embodiments of the disclosure.

In some embodiments, system 100 includes a dental measurement device 102. In some embodiments, system 100 includes one or more display, for example, a display 118 located on dental measurement device 102 and/or a display 124 external to the dental measurement device.

Optionally, in some embodiments, dental measurement device includes a stylus 116 which, in some embodiments, extends outwards from a body of the dental measurement device.

In some embodiments, dental measurement device 102 includes an imager which is e.g. configured to collect images of portions of a patient's mouth and/or of stylus 116. In some embodiments, the imager includes one or more camera 106, which, in some embodiments, is configured to collect images of dental object/s in proximity to the dental measurement device. In some embodiments, the imager includes a final optical element 108. In some embodiments, final optical element 108 is located in a distal end of dental measurement device 102 and/or a portion of dental measurement device sized and/or shaped for insertion into a human mouth. In some embodiments, final optical element 108 is a mirror configured to reflect images to camera 106.

In some embodiments, system 100 includes one or more sensor 120. In some embodiments, sensor/s 120 includes one or more position and/or orientation and/or proximity sensor (e.g. gyroscope and/or accelerometer and or electromagnetic sensor) and/or one or more contact sensor (e.g. strain gauge) and/or one or more sound sensor (e.g. microphone). In some embodiments, sensor/s 120 include one or more inertial measurement unit (IMU) which includes, for example, one or more accelerometer and/or gyroscope and/or magnetometer.

In some embodiments, system 100 includes one or more processor 111. In some embodiments, dental measurement device 102 includes a processor 110.

In some embodiments, one or more of processors 110, 111 are configured to receive images collected by camera 106 and to generate a 3D model (e.g. of at least a portion of a patient's mouth) from the collected images.

Figure 2:
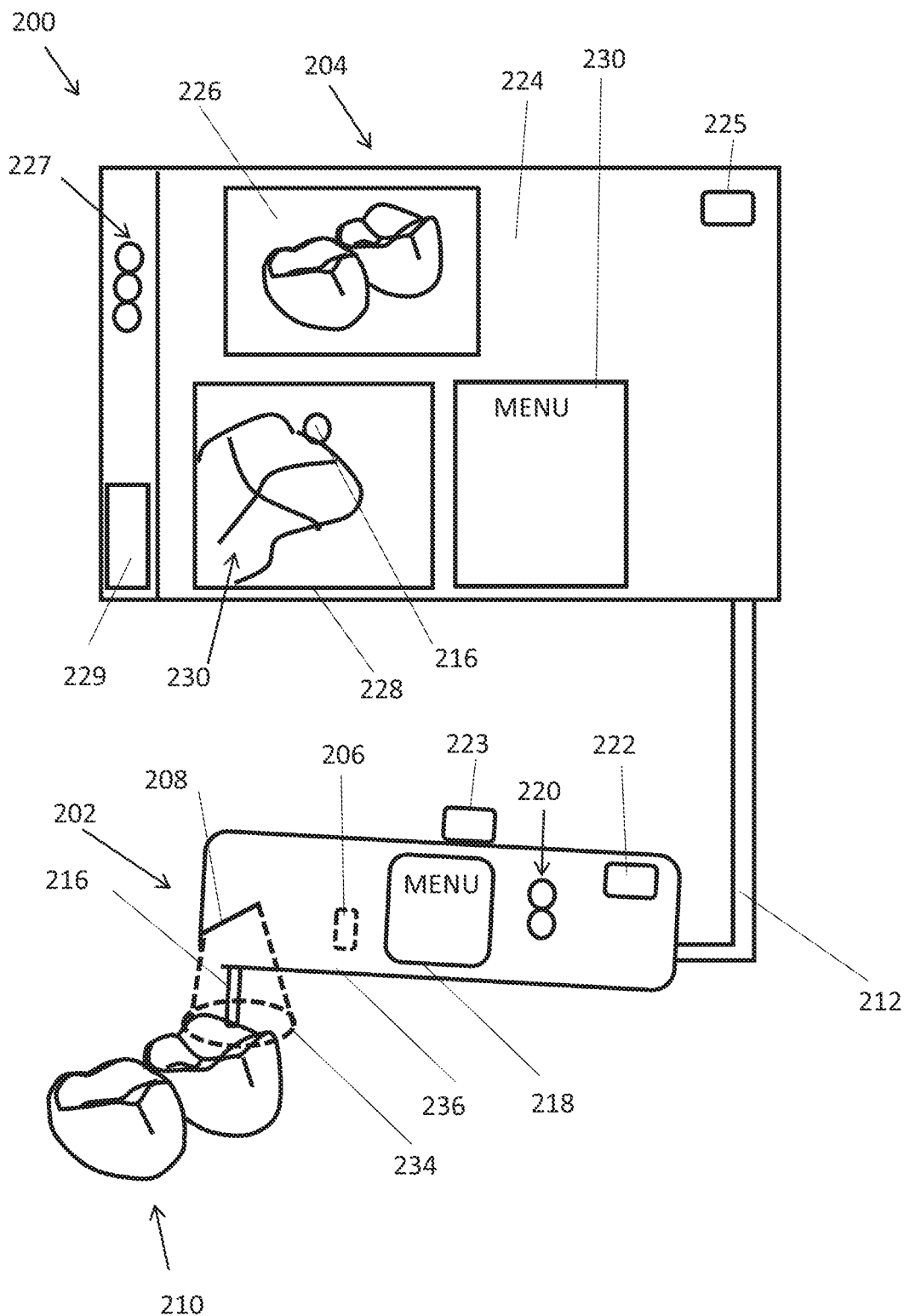
FIG. 2 is a simplified schematic of an exemplary system, according to some embodiments of the disclosure.

FIG. 2 is a simplified schematic of an exemplary system 200, according to some embodiments of the disclosure.

In some embodiments, system 200, includes one or more dental measurement device 202.

In some embodiments, dental measurement device 202 is an intraoral scanner (IOS) including one or more optical sensor 206 (e.g. one or more camera) with a field of view (FOV) 234. In some embodiments, optical sensor 206 receives images reflected towards the sensor by a mirror 208.

For example, in some embodiments, an IOS projects structured light onto a portion of the mouth to be measured (where structured light is, for example, light with a pattern, where the pattern is known). In some embodiments, the IOS collects visual images of the mouth portion illuminated with the structured light, extracts a pattern of the structured light incident on the mouth portion, and infers 3D information regarding topography of the mouth portion from deformation of the pattern of the structured light incident on the mouth portion as compared with the structure of the projected light.

For example, in some embodiments, an IOS (alternatively or additionally to using structured light) includes more than one camera where the cameras are orientated on the IOS such that the cameras have different views of the mouth portion. In some embodiments, 3D information regarding topography of the mouth portion is inferred by comparing the different views of the mouth portion collected by the cameras.

For example, in some embodiments, an IOS (alternatively or additionally to using structured light and/or different camera views) collects 3D measurements using confocal techniques where, for example, camera/s of the IOS collect images of a mouth portion at different distances from the mouth portion (e.g. by focusing the camera/s at different focal distances) and 3D information regarding topography of the mouth portion is inferred from the collected images.

In some embodiments, e.g. for one or more of the IOS data collection techniques described above, inferred 3D information is used to generate a 3D model of the mouth portion. In some embodiments, the model includes a 3D surface of the mouth portion. In some embodiments, the 3D information includes discrete data points.

In some embodiments, an IOS is moved around inside a patient's mouth to collect measurements of different portions of the mouth. In some embodiments, the measurement data, from different portions of the mouth is combined to create a single 3D model (which, for example, includes a 3D surface) of at least a portion of the mouth.

In some embodiments, system 200 includes a control console 204. In some embodiments, dental device 200 is connected to control console 204 by an electrical power and/or data connection 212. Alternatively, or additionally, in some embodiments, a data connection between control console 204 and measurement device 202 is wireless.

Optionally, in some embodiments, dental measurement device 202 includes a stylus 216. In some embodiments, stylus 216 is sized and/or shaped for insertion between a tooth and surrounding gingiva, for example, without damaging the gingiva. In some embodiments, optical images collected by sensor 206 include images of at least a portion of stylus 216. In some embodiments, stylus 216 extends away from a body 236 of dental measurement device 202. In some embodiments, stylus 216 extends into FOV 234 of optical sensor 206.

In some embodiments, a processor (e.g. within measurement device 202 and/or a control console processor 214) uses optical data collected by sensor 206 to generate a model of a portion of a mouth 210 being measured, for example, as described in U.S. Pat. No. 9,454,846, which is herein incorporated in its entirety by reference.

In some embodiments, dental measurement device 202 includes one or more user interface: In some embodiments, dental measurement device 202 includes one or more visual display 218, for example, a LCD display, a touch and/or flexible screen, a display including one or more light (e.g. LED, OLED). In some embodiments, dental measurement device 202 includes one or more button and/or switch 220. In some embodiments, dental measurement device 202 includes one or more speaker 222 and/or microphone.

In some embodiments, a dental device (e.g. a dental measurement device, a dental tool) includes a flexible display, e.g. a flexible display screen. In some embodiments, the flexible display is mounted on a non-planar topography of the dental device. For example, in some embodiments, a flexible display is wrapped around a portion of the dental device, e.g. covering more than one side of the device. For example, in some embodiments, a flexible display is mounted on at least a portion of the dental device (e.g. of a housing of the dental measurement device) which includes a convex and/or concave portion and/or a protrusion and/or indentation.

Alternatively or additionally, in some embodiments, control console 204 includes one or more user interface. For example, one or more visual display 224 (e.g. LCD display, touch screen, light). In some embodiments, control console includes one or more button or switch 227 and/or one or more speaker 229 and/or microphone. Optionally, in some embodiments, control console 200 includes a connection for one or more additional input device, for example, a mouse, a keyboard (not illustrated).

In some embodiments, one or more of dental measurement device 202 and control console 204 include a processor and/or memory and/or are connected to an external processor and/or memory. For example, in some embodiments, the system accesses externally collected data, for example, data collected by another measurement system e.g. x-ray and/or CT and/or MRI and/or ultrasound measurement data. For example, in some embodiments, the system transmits data externally, for example, measurement data is sent for manufacture of a prosthetic.

In some embodiments, control console 204 displays (e.g. on display 224) one or more of, a model of a portion of a mouth 226, one or more image 228 (e.g. collected by optical sensor 206), a control menu 230.

In some embodiments, control menu 230 is configured to receive user control instructions regarding operation of the dental measurement device and/or control console (e.g. what is displayed by the control console). In some embodiments, display 224 is a touch screen and item/s on control menu 230 are selected by a user touching the screen. Alternatively or additionally, in some embodiments, a user controls a selection from control menu 230 with an input device e.g. using one or more of button/s 227, a mouse, a keyboard, movement and/or orientation and/or position of dental measurement device 202.

In some embodiments, visible in image 228 are patient mouth portion/s 232 and/or stylus 216 of the dental measurement device. In some embodiments, image 228 includes images collected by optical sensor 206 e.g. real time video of collected optical images. In some embodiments, image 228 displays collected optical data augmented with (e.g. overlaid by) additional information e.g. feedback regarding quality of data and/or marking added by a user (e.g. as described regarding FIG. 19 and FIG. 20 herein below).

In some embodiments, system 200 lacks a control console and/or display which is external to dental measurement device 202, for example, dental measurement device 202 including user interfaces for control of the device and display of information to a user.

In some embodiments, system 200 includes one or more camera configured to collect images of a user, for example, of a user's face and/or eye/s (e.g. for estimation of a user's line of sight). In some embodiments, the camera is located on the dental measurement device 223. Alternatively or additionally, in some embodiments, the camera is located on another portion of the system and/or within a room in which the system is located, e.g. camera 225 located on display 224. Where, for example, in some embodiments, images collected by the camera include the dental measurement device and the user (e.g. for estimation of user line of sight with respect to the dental measurement device). In some embodiments, the camera is a 3D camera.

Exemplary Collection of Dental Measurements According to Some Embodiments

Figure 3:
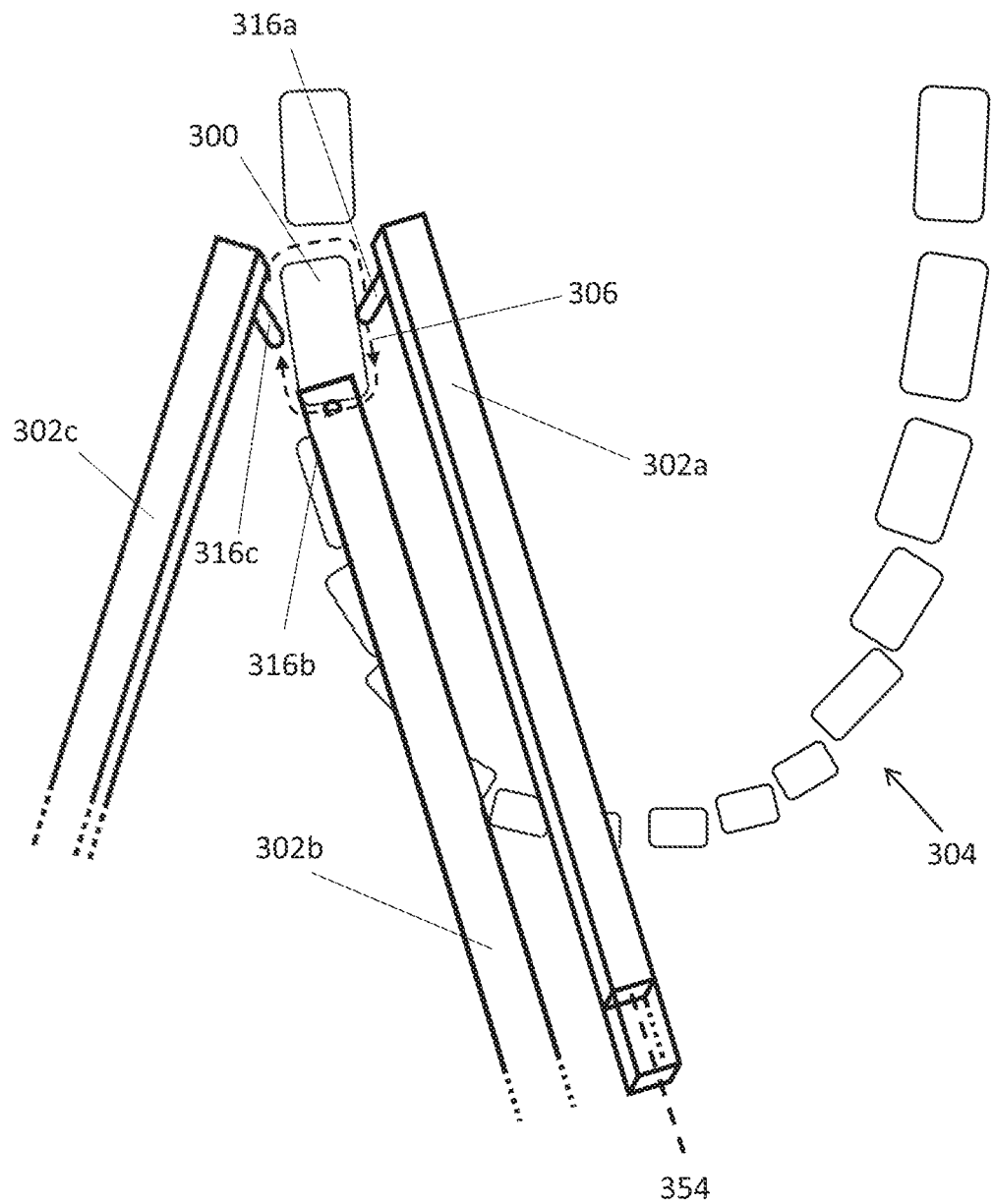
FIG. 3 is a simplified schematic of exemplary positions of a dental measurement device during measurement of a dental feature within a jaw, according to some embodiments of the disclosure.

FIG. 3 is a simplified schematic of exemplary positions of a dental measurement device during measurement of a dental feature 300 within a jaw 304, according to some embodiments of the disclosure.

In some embodiments, dental feature 300 is a tooth, for example, a tooth prepared for attachment thereto of a dental prosthetic (e.g. crown, bridge). In some embodiments, a dental feature 300 is measured by moving a dental measurement device around the dental feature, movement of the device as, for example, illustrated by sequence of position of dental device from 302a to 302b to 300c. In some embodiments, dental device 302a-c includes a stylus 316a-c and measurement includes contacting the stylus to the tooth surface to be measured. In some embodiments, the dental feature is scanned along a path 306 around the tooth where the stylus contacts sub-gingival portions of the tooth along path 306.

In some embodiments, (e.g. as the stylus is moved around the tooth) the stylus is scanned in a coronal apical direction covering sub-gingival and/or supragingival portions of the tooth. In some embodiments, coronal apical movements are automatically actuated (e.g. by one or more actuator) while, for example movement of the dental device body is manually guided by a user grasping the device. Alternatively, both movements are performed manually by a user.

In some embodiments, for example, as illustrated in FIG. 3, the dental measurement device is tilted (e.g. by rotating the device about a central long axis 354 of the device) during measurements. Tilting, for example, potentially improves visibility of the stylus and/or accessing of the tooth surface (e.g. sub-gingival surface) with the stylus. For example, as illustrated in difference in visibility of stylus 316c and 316a where the device is tilted to the view of device 302b where stylus 316b is completely obscured from view by the body of the dental device 302b.

In some embodiments, the dental measurement device is used to measure distances within a patient's mouth. For example, in some embodiments, in a caliper operation mode, a user contacts a stylus to two different mouth portions and a distance between the portions is estimated using collected images and/or a 3D model of a mouth portion and/or position sensor data. For example, to measure two sides of a tooth and/or an implant and/or distance between two implants and/or teeth. In some embodiments, measured distance is a straight line distance between the two points. In some embodiments, the measured distance is a distance between the two points along a tooth contour, which is, for example, estimated using a tooth surface of a 3D model. In some embodiments, the system is put into caliper operation mode by one or more of a user selection at a display, a user performing a gesture, a user entering an instruction using a user interface.

Exemplary Method of Dental Measurement According to Some Embodiments

Figure 4:
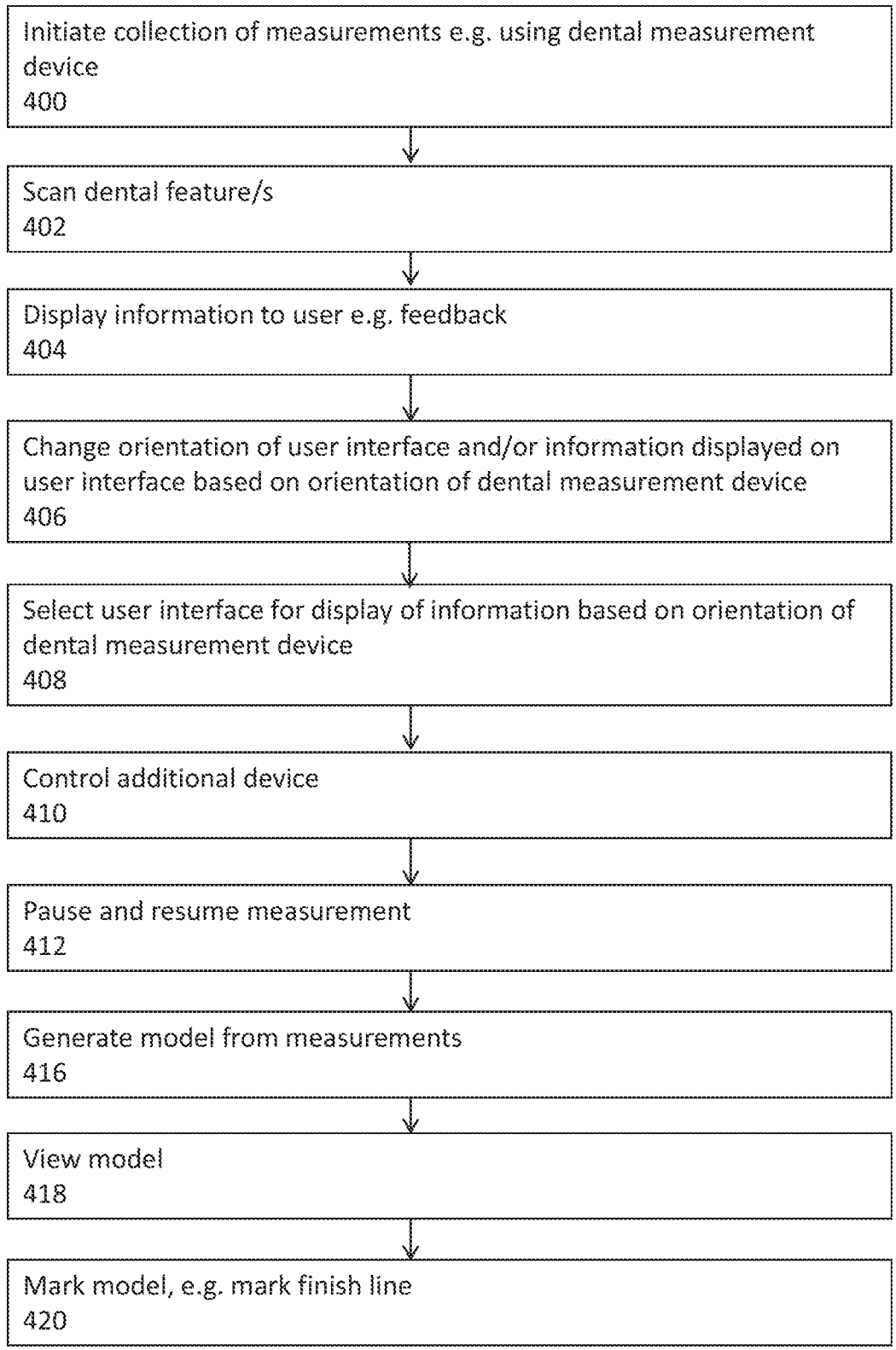
FIG. 4 is a flow chart of a method of collecting dental measurements, according to some embodiments of the disclosure.

FIG. 4 is a flow chart of a method of collecting dental measurements, according to some embodiments of the disclosure.

In an exemplary embodiment, dental measurements are collected of one or more prepared tooth, the measurements, for example, in some embodiments, being used in construction of a dental prosthesis e.g. crown, bridge.

At 400, in some embodiments, dental measurements using a dental measurement device (e.g. 202 FIG. 2, 1502 FIG. 15A) are initiated.

In some embodiments, measurements are initiated by a user inputting into the system one or more user control input.

For example, in some embodiments, a start to collection of measurements is initiated using a user interface on a control console (e.g. 230 and/or 227 and/or touch screen 224) and/or using an interface on the dental measurement device (e.g. 218 and/or 220, FIG. 2).

Additionally, or alternatively, in some embodiments, a user initiates a start to collection of measurements by selecting an option at a display (e.g. selecting an option of menu 230) by movement and/or orientation and/or position of dental measurement device 202.

Additionally, or alternatively, in some embodiments, a user initiates a start to collection of measurements by performing one or more gesture with the dental measurement device.

For example, in some embodiments, the user performs a contact gesture, for example by tapping and/or contacting a portion of the dental measurement device to a mouth portion (e.g. a tooth surface).

Figure 17:
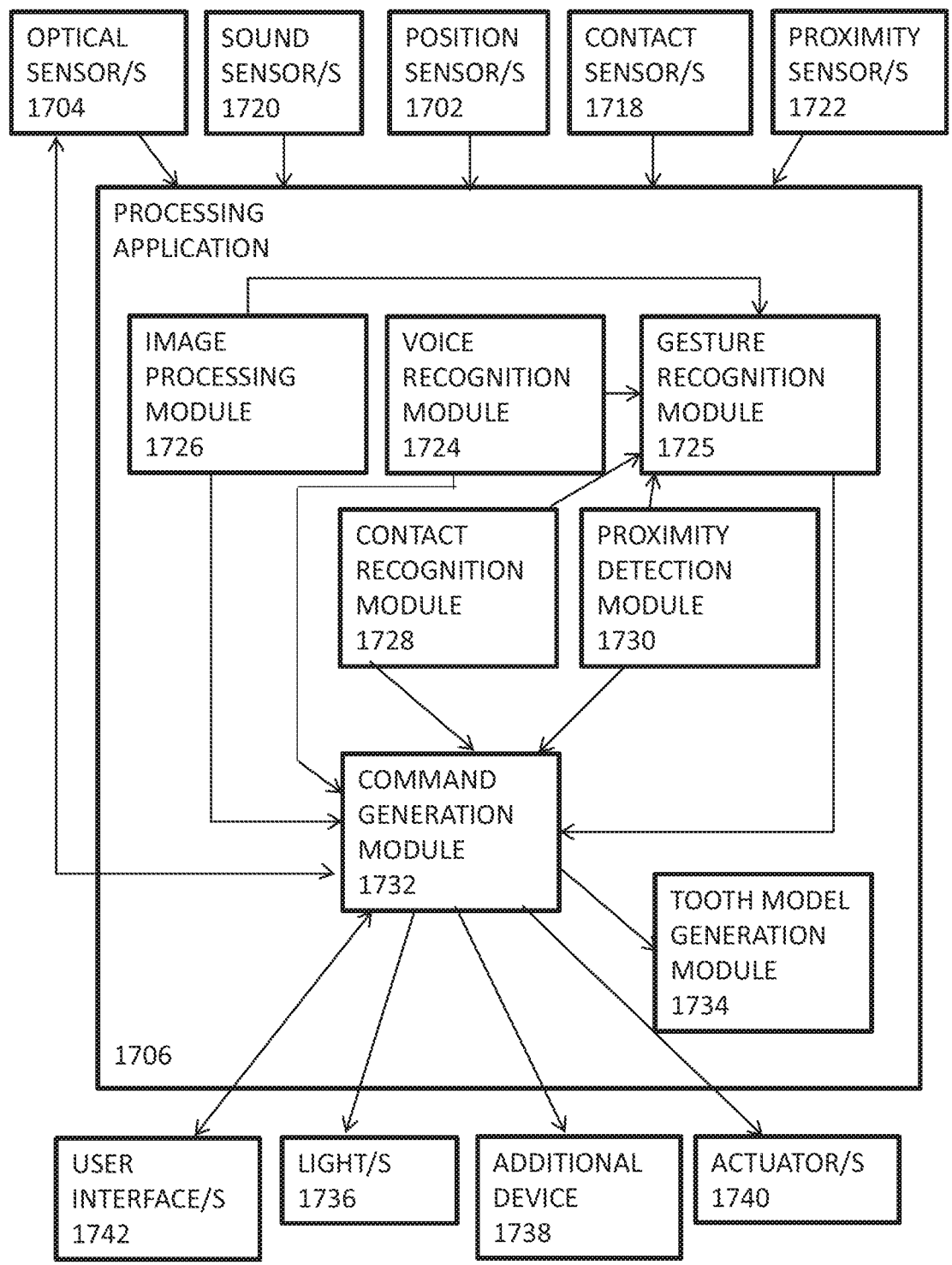
FIG. 17 is a simplified block diagram of a control infrastructure for a dental measurement system, according to some embodiments of the disclosure.

In some embodiments, a gesture which initiates a start to collection of measurements is a detected level of contact (e.g. above a threshold pressure) between a stylus of the measurement device and mouth (e.g. tooth) surface Additionally, or alternatively, a contact gesture and/or a movement gesture (e.g. as described elsewhere in the document, e.g. with reference to FIG. 17) initiate a start to collection of measurements.

In some embodiments, more than one control input is inputted by a user to initiate a start to measurements. For example, one or more different type of control input. For example, in some embodiments, both a movement and a contact gesture are detected to initiate a start of measurements, for example, turning the measurement device followed by tapping the measurement device on a tooth surface. For example, in some embodiments, a user switches the dental measurement device on (e.g. using a user interface on the dental measurement device) and then performs a gesture to start measurements (e.g. tapping a stylus of the measurement device on a tooth surface).

In some embodiments, initiation of measurement is automatic or partially automatic. For example in some embodiments (optionally after a user has inputted a control input instructing a start to measurements) the device automatically starts collecting measurements e.g. when the device sensor/s recognize a pre-determined situation. For example, when device sensor/s recognize a sufficient contact between a device stylus and a tooth and/or when image processing of images collected by the dental measurement device indicate that the device is in position, with respect to dental object/s, appropriate for measurement of the object/s.

At 402, in some embodiments, dental measurements are collected by scanning of dental feature/s with the dental measurement device (e.g. as described regarding FIG. 3 and/or as described in U.S. Pat. No. 9,454,846).

At 404, in some embodiments, information is displayed. In some embodiments, the dental measurement displays an indication of a mode or status of the system and/or measurement device, for example, an indication as to whether the dental measurement device is in a mode where it is collecting and/or capable of collecting measurements, for example, an indication as to whether the dental measurement device is in a mode where it is used to control and/or add to previously collected data (e.g. a "mark model" mode e.g. as described regarding FIGS. 19-20)

In some embodiments, during and/or after collection of measurements, feedback is generated and/or displayed. Where feedback is, for example, regarding whether sufficient measurements have been collected, e.g. sufficient density of measurement e.g. for construction of a dental prosthetic and/or for alignment of collected data with another dataset (e.g. as described in U.S. Patent Application No. 62/528,475 which is herein incorporated by reference). In some embodiments, feedback to a user is displayed visually by a user interface on the dental measurement device.

In some embodiments, feedback is displayed during measurement with the dental measurement device and a user is potentially guided by the feedback during performance of measurements.

In some embodiments, for example, in addition or alternatively to a user controlling movement of the measurement device by directly viewing visible portions of the mouth and/or dental device, a user controls movement of the measurement device by viewing visual feedback displayed on one or more displays and/or audio feedback broadcast by one or more speaker, and/or haptic feedback. In some embodiments, visual feedback is displayed on one or more surface of the dental measurement device. In some embodiments, audio feedback is broadcast by one or more speaker incorporated into the dental measurement device. In some embodiments, haptic feedback is provided by one or more actuator within the dental measurement device. Alternatively or additionally, in some embodiments, visual feedback is displayed on an additional display, for example a display of a control console (e.g. 204 FIG. 2).

In some embodiments, an orientation of feedback displayed is based on an orientation of a dental object (e.g. a dental object being measured) with respect to the feedback display e.g. as described and/or illustrated regarding FIGS. 8A-D.

In some embodiments, visual feedback includes images collected by the dental measurement device. For example, in some embodiments, displayed images including portion/s of the patient's mouth and/or of a stylus of the measurement device are displayed, potentially assisting a user in positioning of the dental measurement device and/or stylus e.g. during measurement.

Figure 13A:
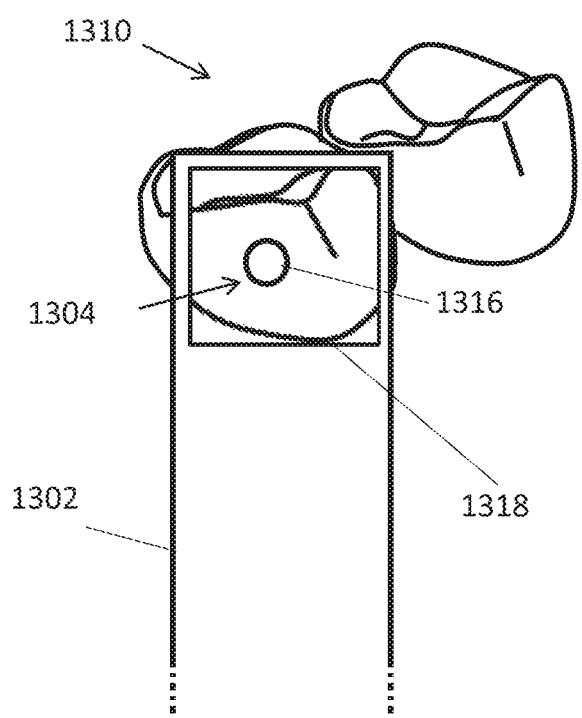
FIG. 13A is a simplified schematic of a dental measurement device displaying an image of an obscured portion of a patient's mouth, according to some embodiments of the disclosure.
Figure 13B:
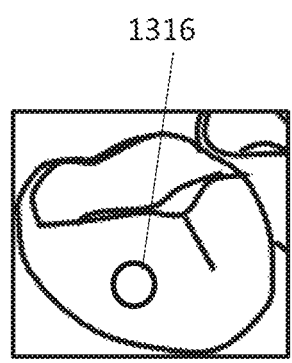
FIG. 13B is a simplified schematic of an image collected by a dental measurement device, according to some embodiments of the disclosure.
Figure 13C:
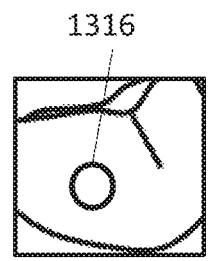
FIG. 13C is a simplified schematic of an obscured portion of the image of FIG. 13A, according to some embodiments of the disclosure.

In some embodiments, processed images are displayed to a user, for example, images augmented with additional information (e.g. feedback information is displayed with collected images e.g. overlaid onto collected image/s), for example, sized images are displayed (e.g. as described regarding FIGS. 13A-C and/or 14).

In some embodiments, instructions to a user are displayed, for example, on a display (e.g. of the dental measurement device and/or an external display). Where, for example, in some embodiments, instructions to a user are based on generated feedback. For example, in some embodiments, instructions to a user are generated based on user inputs to the system and/or collected measurement data. For example, in some embodiments, instruction to a user include safety alert/s.

In some embodiments, feedback and/or instructions to a user include sound produced by one or more speaker located on the dental measurement device and/or on a control console (e.g. 229 and/or 222). For example, in some embodiments, the dental measurement device provides an audio cue when sufficient data has been collected. Exemplary audio cues include producing a tone and/or noise and/or changing an existing audio signal e.g. changing a pitch of a repeated sound, changing a frequency of repetition of a repeated sound. In some embodiments, audio feedback includes one or more feature as described regarding FIG. 23.

At, 406, in some embodiments, for example during collection of measurements with the dental measurement device, an orientation of the dental device changes.

In some embodiments, an orientation of the dental measurement device changes with respect to a user line of sight e.g. as illustrated and described with respect to FIG. 3.

In some embodiments, feedback displayed is based on an orientation of the dental measurement device with respect to a user, e.g. based on which portion/s of the device are visible to the user. In some embodiments, feedback includes image/s collected by the dental measurement device.

In some embodiments, feedback is distorted and/or changed based on visibility of the display on which the feedback is displayed to the user. For example, in some embodiments, tilting of the dental measurement device obscures a portion of a display (e.g. obscured by the device itself) and, in some embodiments, feedback is then displayed on (e.g. only on) the portion of the display visible to the user.

Figure 9A:
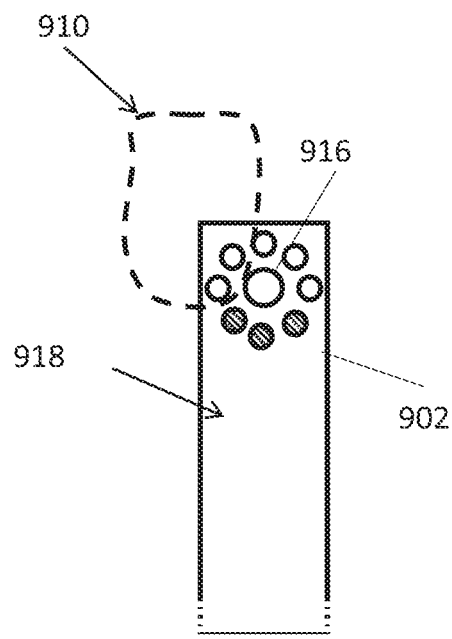
FIGS. 9A-B are a simplified schematic of a dental measurement device including a feedback display measuring a dental object, according to some embodiments of the disclosure.
Figure 9B:
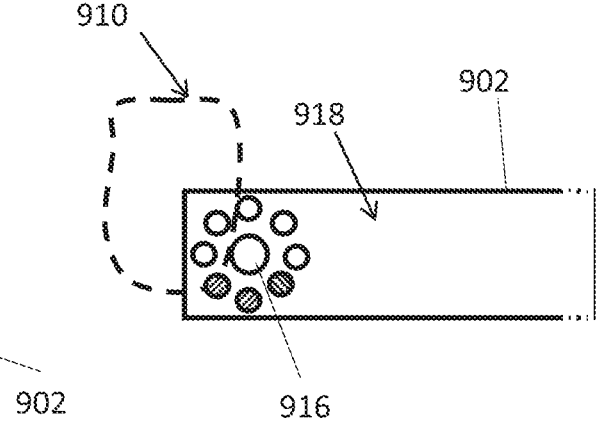

In some embodiments, an orientation of the dental measurement device changes with respect to a dental object being measured e.g. as illustrated and described regarding FIGS. 9A-B.

In some embodiments, an orientation of feedback displayed is based on an orientation of a dental object being measured, for example, in some embodiments, if the dental measurement device changes orientation the feedback is reoriented with respect to the dental measurement device, to maintain an orientation with respect to the dental object being measured (e.g. as illustrated and/or described regarding FIGS. 9A-B).

At 408, in some embodiments, a user interface is selected based on an orientation of the dental measurement device. In some embodiments, a dental measurement device includes a plurality of user interfaces on different portions of the device. In some embodiments, one or more user interface on the dental measurement device is activated and/or deactivated based on an orientation of the dental measurement device. In some embodiments, a user interface on the dental measurement device (e.g. for display of feedback) is selected (e.g. activated) based on the orientation of the measurement device, with respect to a patient's mouth and/or a line of sight of a user. Where the user interfaces, in some embodiments, include one or more of visual user interface/s (e.g. displays), audio user interface/s (e.g. speaker/s), and haptic user interface/s.

At 410, in some embodiments, one or more additional device or tool (e.g. a suction tool, e.g. a drill) is controlled (e.g. switched on and/or switched off). For example, using the dental measurement device. For example, by the user inputting, using the dental measurement device, one or more user control input.

In some embodiments, a user interface on the dental measurement device is used to control one or more additional device.

Additionally or alternatively, in some embodiments, a user performs one or more gesture using the dental measurement device to control one or more additional device.

For example, in some embodiments, by performing a contact gesture (where contact, in some embodiments, is between the dental measurement device and the additional device) and/or movement gesture, e.g. with respect to the device. For example, in some embodiments, an additional device (e.g. suction device) is activated by a user gesturing towards the additional device (e.g. pointing at the additional device using a stylus of the dental measurement device) and/or contacting the additional device (e.g. with a dental measurement device stylus).

In some embodiments, a gesture includes a detected proximity between the additional device and the dental measurement device.

For example, the additional device only activating at sufficient proximity to the dental measurement device, for example, the additional device automatically activating at sufficient proximity to the dental measurement device. In an exemplary embodiment, a suction device automatically activates when in sufficient proximity to the dental measurement device (e.g. within 3 cm, or 2 cm, or 1 cm, or 0.5 cm, or lower, or higher, or intermediate distances, of a distal end of the dental measurement device).

In some embodiments, proximity is detected using one or more position sensor. In some embodiments, proximity is detected by using one or more optical sensor, for example, by identifying (e.g. using machine vision) an additional device from images collected using the dental measurement device. For example, in some embodiments, when an additional device appears in a FOV of camera/s of the dental measurement device, it is identified (e.g. using image processing). In some embodiments, the additional device, once identified, is activated e.g. by the system sending a control signal to the additional device.

In some embodiments, an additional device is activated based on collected images (e.g. images collected by the dental measurement device). For example, in some embodiments, a suction device is activated when excessive fluids are identified from collected images (e.g. using image processing).

At 412, in some embodiments, measurements are paused, for example, in some embodiments, a user pauses measurement to evaluate collected measurements e.g. by viewing data collected using one or more user interface.

In some embodiments, a pause user control input is entered by a user into a user interface and/or by the user performing one or more gesture with the dental measurement device. Alternatively or additionally, in some embodiments, the system pauses collection of measurements automatically, for example, upon sensed inputs. For example, in some embodiments, if the dental measurement device loses contact and/or is moved below a threshold proximity with the patient's mouth.

In some embodiments, optionally after other steps are carried out, the user resumes measurements with the dental measurement device e.g. by entering user control input into a user interface and/or by performing a gesture with the dental measurement device. In some embodiments, the system automatically resumes measurements once the dental measurement device is positioned in a position where the measurements were paused.

At 416, in some embodiments, a model (e.g. a 3D model) of at least a portion of the patent's mouth is generated using collected measurement data. For example, as described in U.S. Pat. No. 9,454,846.

At 418, in some embodiments, a user views the generated model, on a user interface. In some embodiments, the user views the model on a dental measurement device user interface, e.g. as part of feedback displayed to the user. Optionally the model is displayed to the user during collection of measurements, where, for example, the model is generated incrementally as measurement is collected, a partial model being displayed and/or updated.

In some embodiments, the model is displayed on a display not mounted on the measurement device, e.g. display 124 FIG. 1, 224 FIG. 2.

Figure 18:
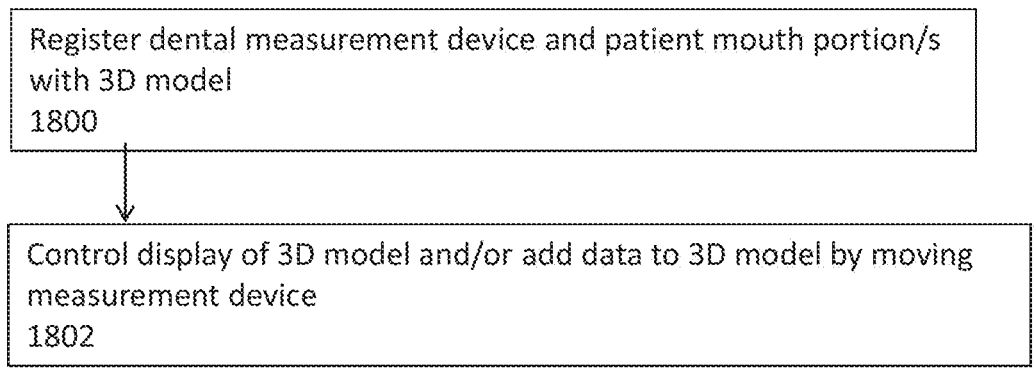
FIG. 18 is a flow chart of a method of display control, according to some embodiments of the disclosure.

In some embodiments, a user manipulates display of the model using one or more dental measurement device user interface e.g. as illustrated by and/or described regarding FIG. 18. In some embodiments, display of the model is manipulated by a movement (e.g. position and/or orientation in space) of the dental measurement device. For example, in some embodiments, after and/or during a scan, a user checks the 3D model by viewing the model from more than one angle (e.g. by moving the dental measurement device). For example, to visually determine whether sufficient measurements have been collected (e.g. extent of mouth portion/s measured). For example, to check that there are no missing tooth portions which have not been measured. For example, to check that the correct teeth have been scanned.

In some embodiments a user inputs a command at a user interface, for example, presses a button (e.g. located on the dental measurement device) to freeze movement of the 3D model. In some embodiments, a user inputs a command at a user interface to start a mode where movement of the dental measurement device controls orientation of the displayed 3D model. For example, by pressing a button on the dental measurement device, and, in some embodiments, exiting the mode, by releasing and/or re-pressing the button.

Figure 19:
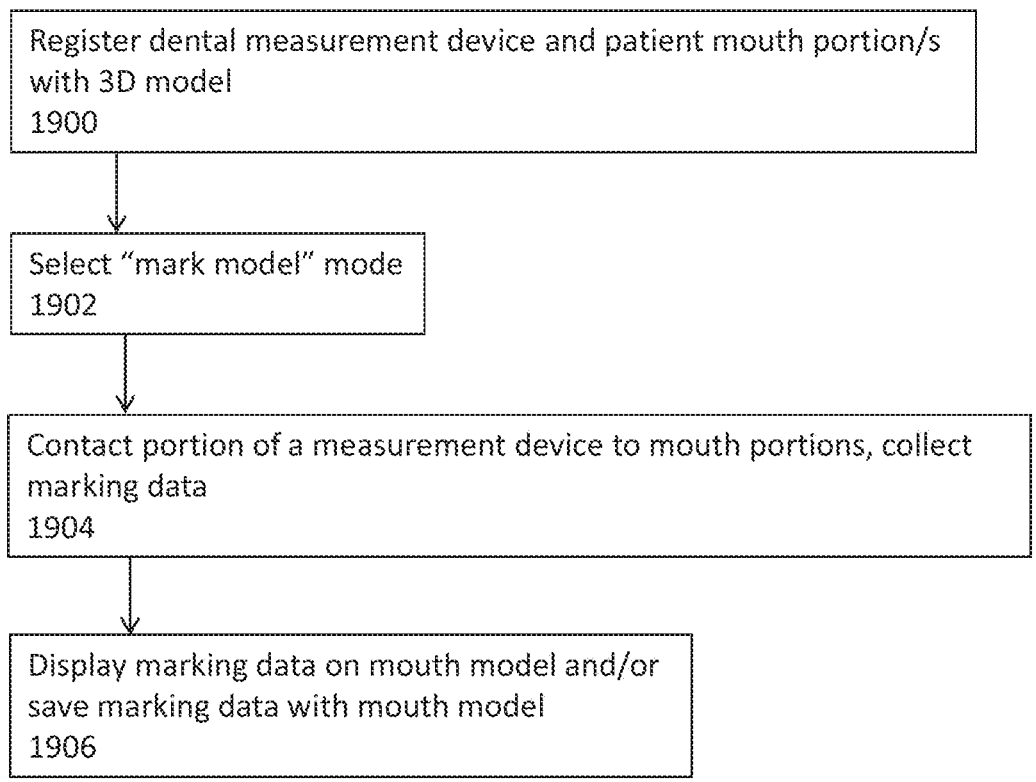
FIG. 19 is a flow chart of a method of adding data to a model of at least a portion of a mouth, using a dental measurement device, according to some embodiments of the disclosure.
Figure 20:
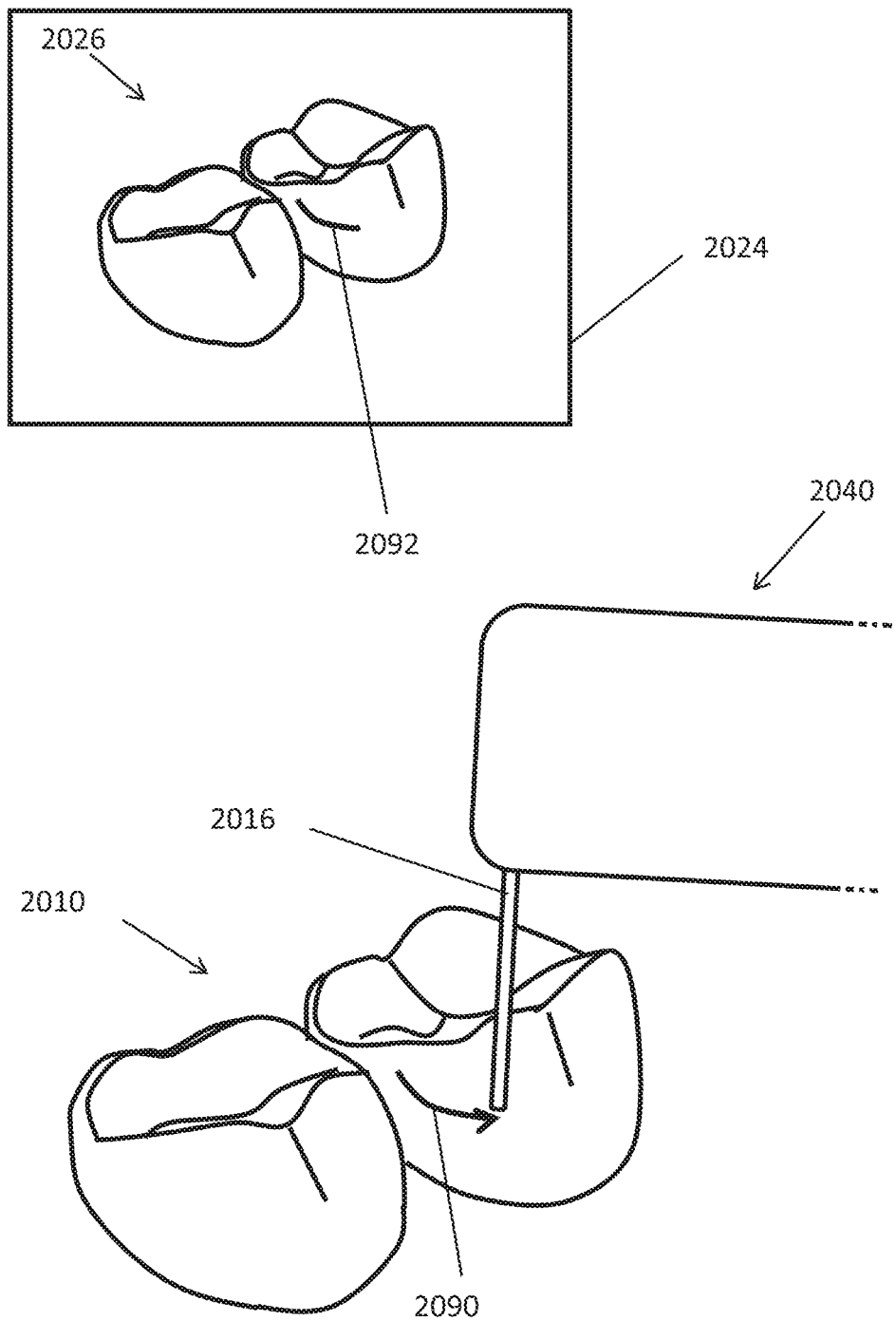
FIG. 20 is a simplified schematic of marking of a tooth model, according to some embodiments of the disclosure.

At 420, in some embodiments, information is added to the model using the dental measurement device e.g. as illustrated by and/or described regarding FIG. 19 and FIG. 20. In some embodiments, the dental measurement device is contacted to one or more portion of a patient's mouth and the position of contact, as aligned with the model, is marked on the model. In some embodiments, a finish line of a prepared tooth is manually delineated using the dental measurement device, for example, the probe is contacted to and scanned around the finish line.

In some embodiments, a manually delineated finish line is corrected, for example, by a processor, e.g. based on the manually delineated finish line and additional measurement/s of the tooth, e.g. a 3D model generated from dental measurement device data and/or other data e.g. CT, MRI, ultrasound. In some embodiments, the corrected finish line is displayed to a user.

In some embodiments, a user manually alters and/or corrects a finish line using the dental measurement device, e.g. by controlling a cursor location using movement and/or orientation and/or position of the dental measurement device to adjust the finish line.

Exemplary User Interface Control According to Some Embodiments

Figure 5:
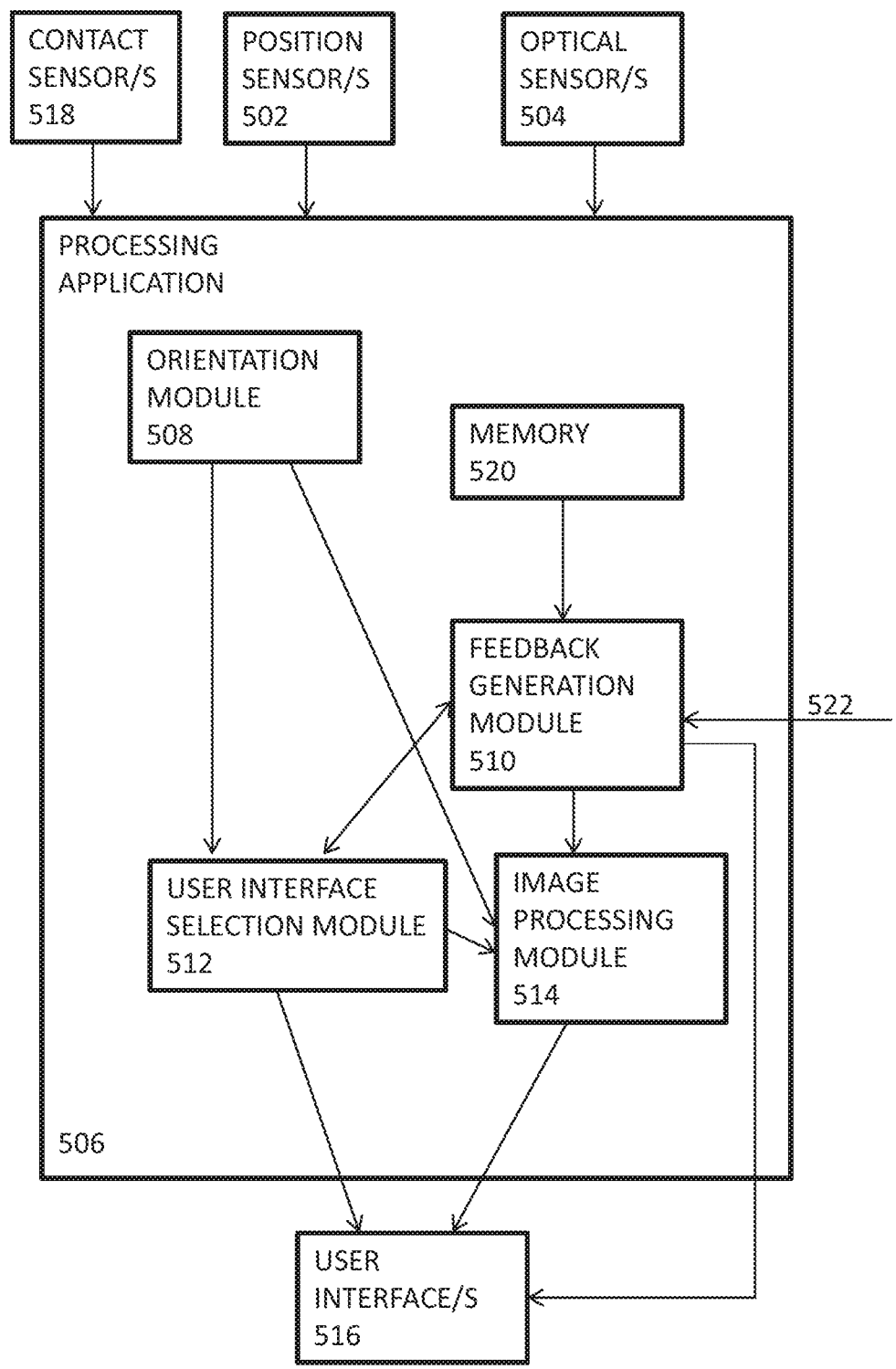
FIG. 5 is a simplified block diagram of a dental measurement system, including a dental measurement device, that displays information to a user, according to some embodiments of the disclosure.

FIG. 5 is a simplified block diagram of a dental measurement system, including a dental measurement device, that displays information to a user, according to some embodiments of the disclosure.

In some embodiments, one or more positon sensor 502 and/or one or more optical sensor 504 supply data to a processing application 506.

In some embodiments, position sensor/s 502 measure one or more of specific force, angular velocity, and magnetic field surrounding the sensor/s. In some embodiments, position sensor/s include one or more IMU, for example, including one or more gyroscope and/or one or more accelerometer, and/or magnetometers. Additionally or alternatively, in some embodiments, position sensor/s 502 include one or more electromagnetic position sensor and/or one or more ultrasonic position sensor.

In some embodiments, the system includes one or more contact sensor 518 which detects contact between a dental device and portions of a patient's mouth, for example, detecting contact and/or strength of contact between a stylus of a dental device (e.g. stylus 216 FIG. 1, 1516 FIGS. 15A-D) and object/s with which the stylus is in contact with (e.g. portion/s of a patient's mouth).

Additionally or alternatively, in some embodiments, the system includes one or more contact sensor 518 which, for example, senses user hold on the device (e.g. user hold on a device handle e.g. handle 1544 FIG. 15A), for example, sensing where a user is contacting the device and/or how strong the contact between the user and the device is.

In some embodiments optical sensor/s 504 include one or more camera located within the dental measurement device. In some embodiments, a device camera is configured to collect images of dental objects being measured. In some embodiments, a device camera is configured to collect images of a user, e.g. a user's eye position. In some embodiments, optical sensor/s 504 include one or more dental measurement system camera external to the dental measurement device, where position of the dental measurement device and/or dental object/s and/or a patient's mouth and/or a user's body portion/s (e.g. hand/s and/or eye/s) are estimated from collected image/s.

In some embodiments, an orientation of the dental measurement device with respect to a dental object is estimated using images including the dental object collected by device camera/s.

In some embodiments, optical sensor/s 504 are configured to collect color measurement/s. In some embodiments, optical sensor/s 504 include one or more camera configured to collect depth measurements. In some embodiments, the camera is configured to collect depth measurements of region/s illuminated by when patterned light.

In some embodiments, one or more of sensors 502, 504, 518 are part of a (e.g. hand-held) dental measurement device (e.g. 202 FIG. 2, 1502 FIGS. 15A-D).

In some embodiments, processing application 506 is hosted by the dental measurement device. Alternatively or additionally, processing application is partially or fully hosted by another device, for example, by a control console (e.g. control console 204 FIG. 2).

In some embodiments, processing application 506 includes an orientation module 508 which receives data from one or more of sensors 502, 504, 518. In some embodiments, orientation module 508, using received data, estimates an orientation of the dental measurement device, in space and/or with respect to one or more other object.

For example, in some embodiments, orientation module 508 estimates an orientation of the dental measurement device with respect to a dental object being measured. For example, in some embodiments, orientation module 508 estimates an orientation of the dental measurement device with respect to a patient's mouth. In some embodiments, the spatial location with respect to a user's line of view (where a spatial location of the user's eye/s is estimated, for example, using image/s collected an additional camera (e.g. which captures image/s of the user's face and/or eyes. In some embodiments, a user's line of view is estimated from images collected by one or more imager where a field of view of the imager includes at least a portion of the user e.g. the user's face and/or eyes. Alternatively or additionally, the estimation is using a position sensor which is e.g. attached to the user.

In some embodiments, the system includes feedback generation module 510, which for example, receives dental measurement data from optical sensor/s 502 and analyses the data, for example, providing feedback on whether data is sufficiently dense (e.g. for a particular process e.g. for constructing a prosthetic) and/or whether there is sufficient data for alignment of the collected data with an additional dataset. Where, for example, additional dataset/s include previously collected and stored data, for example, in a memory 520 and/or where additional data is received through a connection 522 from an external source (not illustrated). Where exemplary external sources include, for example, other measurement systems (e.g. CT data, x-ray data, MRI data, ultrasound data).

In some embodiments, feedback includes an angle of a dental measurement device stylus (e.g. stylus long axis) with respect to a surface of a dental object being measured. In some embodiments, a small angle (e.g. less than 40°, or less than 30°, or less than 20°, or less than 10° or less than 5°, or higher or lower or intermediate values or ranges) between the stylus and the dental object surface degrades measurement accuracy. In some embodiments, feedback includes an indication of a measured (e.g. measured using collected images and/or position sensors) angle between the dental object and the stylus e.g. when the stylus contacts the dental object. In some embodiments, feedback includes an indication that the stylus is below a threshold angle.

In some embodiments, the system includes a user interface (UI) selection module 512. In some embodiments, the system and/or dental measurement device includes more than one user interface and UI selection module selects what information is displayed on each user interface. In some embodiments, UI receives information from orientation module 508, and selects a display based on an orientation of the dental measurement device.

For example, in an exemplary embodiment, orientation module identifies that the dental measurement device is tilted about a long axis of the device (e.g. as illustrated in FIG. 3), and UI selection 512 module selects a user interface visible to a user which is not obstructed from the user's line of view (e.g. by the device). For example, referring to FIG. 15B, in some embodiments, the device is rotated about axis 1554 such that lateral size 1550 is above lateral side 1552 and lateral size 1550 is obscuring the user's view of lateral side 1552. UI selection module 512, for example, selects user interface 1518a for display of information to the user, for example, based on known location of user interface/s and orientation of the device. In some embodiments, UI selection module 512 selects more than one user interface for display of data, in some embodiments UI selection module selects different user interfaces for display of different data.

In some embodiments, the system includes an image processing module 514, for example in some embodiments, images collected by optical sensor/s 504 are processed before being displayed on one or more user interface 516. For example, in some embodiments (e.g. as illustrated in and/or described regarding FIGS. 13A-14) a user interface displays a collected image which has been sized so that the image displayed is of an obscured view (e.g. view of the mouth and/or stylus).

Exemplary Displayed Information According to Some Embodiments

Figure 6:
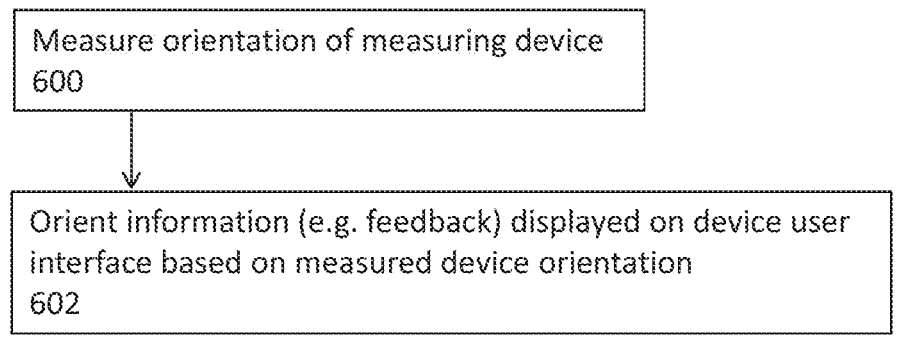
FIG. 6 is a flow chart for a method of display of information, for a dental measurement device, according to some embodiments of the disclosure.

FIG. 6 is a flow chart for a method of display of information, for a dental measurement device, according to some embodiments of the disclosure.

At 600, in some embodiments, an orientation of a dental measurement device is measured.

At 602, in some embodiments information displayed on the dental measurement device, for example, on one or more display, is orientated, based on the measured orientation of the dental measurement device.

In some embodiments, an orientation of a display of the dental measurement device is measured and, in some embodiments, information displayed on the display is oriented based on the measured orientation of the display.

Optionally, in some embodiments, information displayed on and/or by one or more user interface is based on a measured orientation of the dental measurement device with respect to a user's line of sight, for example, is orientated based on the orientation of the dental measurement device.

Additionally or alternatively, in some embodiments, information displayed is based on an orientation of the dental measurement device with respect to one or more dental object. For example, with respect to a dental object (e.g. tooth) being measured. For example, in some embodiments, an orientation of information displayed on a user interface is independent of an orientation of the dental measurement device (e.g. as illustrated and/or described with respect to FIGS. 8A-D and/or FIGS. 9A-B).

Exemplary Display of Feedback with Respect to an Orientation of a Dental Object According to Some Embodiments In some embodiments, feedback is displayed, for example, on a dental measurement device (e.g. 102 FIG. 1, 202 FIG. 2, 1502 FIGS. 15A-D) where the feedback is orientated with respect to a dental object being scanned, for example, a tooth (e.g. prepared tooth).

Figure 7:
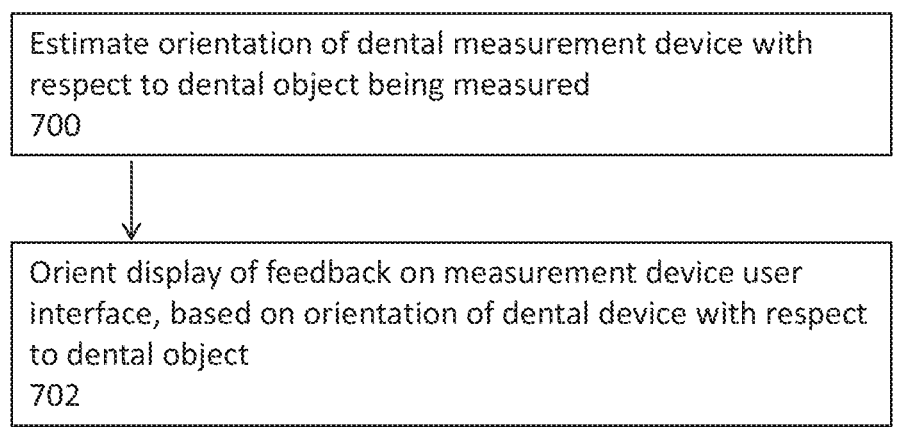
FIG. 7 is a flow chart of a method of feedback display, according to some embodiments of the disclosure.

FIG. 7 is a flow chart of a method of feedback display, according to some embodiments of the disclosure.

At 700, in some embodiments, an orientation of a dental measurement device with respect to a dental object (e.g. tooth) being measured is estimated.

At 702, in some embodiments, an orientation of displayed feedback is with respect to the estimated orientation of the dental measurement device with respect to the dental object being measured. In some embodiments, an orientation of a display of the dental measurement device is measured and, in some embodiments, orientation of the displayed feedback is additionally based on the measured orientation of the display.

FIGS. 8A-D are simplified schematics of a dental measurement device 802 including a feedback display 818 as the dental measurement device is scanned around a dental object 810, according to some embodiments of the disclosure.

A potential advantage of feedback display 818 being located on dental measurement device 802 is user ability to view the dental measurement device and/or patient's mouth and the feedback display in a same region of space and/or without turning of the user's head. A further potential advantage is increased intuitively of spatial feedback when the feedback is displayed in close proximity (e.g. within 1 cm of) to the dental object being measured.

In some embodiments, the dental object is a tooth 810, e.g. a tooth prepared to receive a dental prosthetic.

Figure 8A:
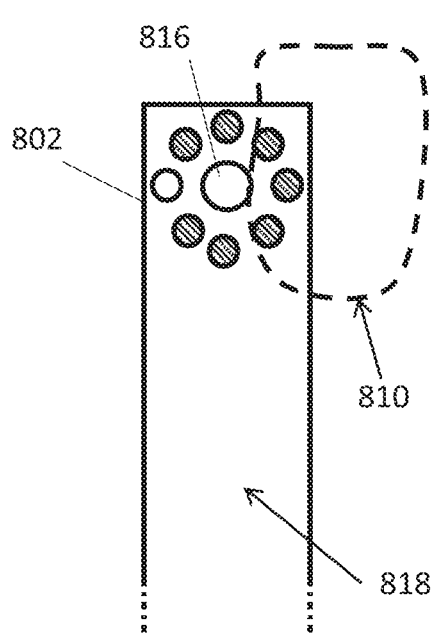
FIGS. 8A-D are simplified schematics of a dental measurement device including a feedback display as the dental measurement device is scanned around a dental object, according to some embodiments of the disclosure.
Figure 8B:
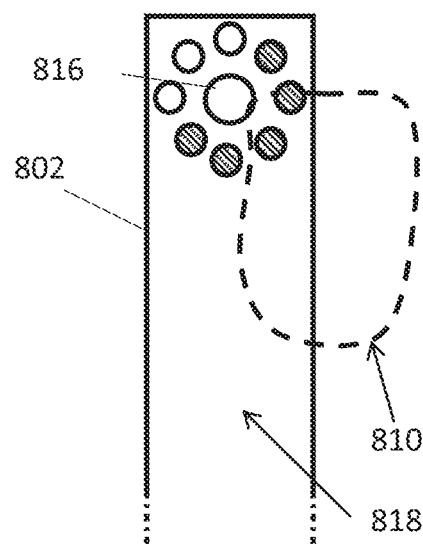
Figure 8C:
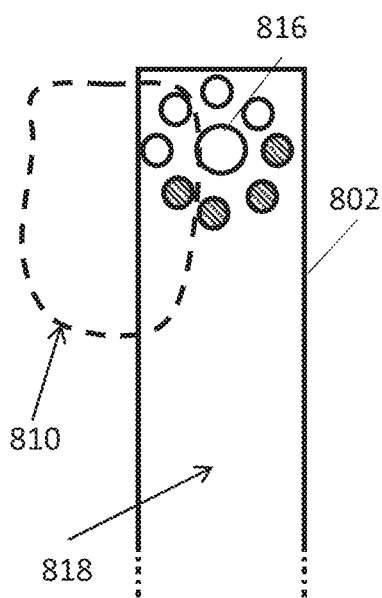
Figure 8D:
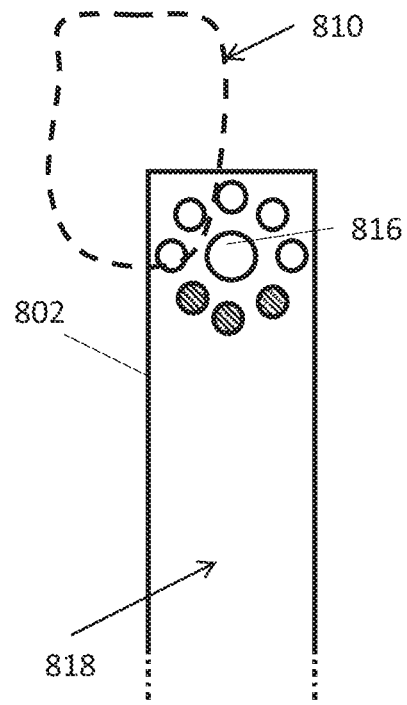

In some embodiments, FIG. 8A shows a start of measurement of dental device 802, FIGS. 8B-D showing the movement of the device around tooth 810 in a clockwise direction. In some embodiments, as the dental device is moved around tooth 810, data is collected and feedback display 818 indicates which areas of the tooth have been measured with respect to the tooth 810. Where, on FIGS. 8A-D shaded areas of the feedback display 818 indicate that measurement has not been collected and unfilled areas indicate that data has been collected, for a portion of the tooth corresponding to the position indicated on the feedback display.

In some embodiments, dental measurement device 802 includes a stylus 816 and measurements are collected by contacting the stylus to surfaces of the dental object being measured. In some embodiments, FIGS. 8A-D illustrate measurement of sub-gingival portions of tooth 810 where stylus 816 is inserted between a surface of tooth 810 and surrounding gingiva. In some embodiments, the stylus is scanned around the tooth (e.g. as illustrated by FIGS. 8A-D) while coronal apical movements are made with the stylus while in contact with tooth 810.

In some embodiments, feedback display 818 includes lights (e.g. LEDs) where, for example, in some embodiments, each circle of feedback display 818 is a light which is, for example, illuminated to indicate that measurement has been collected, e.g. for a corresponding portion of tooth 810. In some embodiments feedback display 818 includes lights with different colors, and/or lights where each light has more than one color illumination option. In some embodiments, a color of illuminated light/s displays information (e.g. to a user). For example, in some embodiments, a first color indicates that sufficient measurement has been collected for a region, a second color indicates that measurement has been collected for a region but that it is insufficient and a third color indicates that measurement has not been started for a region. For example, in some embodiments, red light indicates an area which has not scanned, yellow indicates an area which has been partially scanned and green indicates a fully scanned area.

In some embodiments, e.g. for feedback to be displayed, the dental object being measured is mapped to the feedback display. For example, where the feedback display does not have the same shape as the dental object being measured (e.g. as illustrated in FIGS. 8A-D) and/or the feedback display does not have as high a resolution as measurements of and/or generated feedback for the dental device.

In some embodiments, displayed feedback is a display of a 3D model of the tooth where the display is updated as the model is generated (e.g. as measurements of tooth 810 are collected). In some embodiments, the model feedback display 818 is a screen (e.g. LCD display). In some embodiments, display is of images, e.g. collected by the dental measurement device.

Figure 8E:
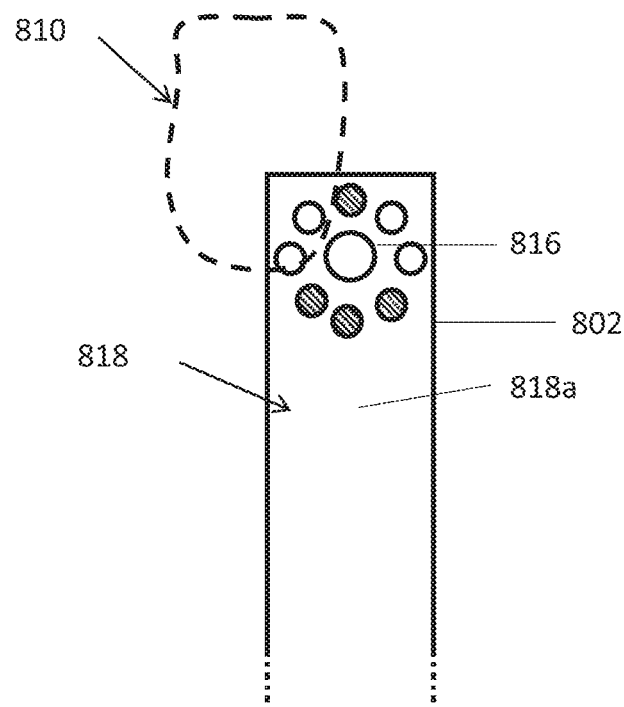
FIG. 8E is a simplified schematic of a dental measurement device including a feedback display measuring a dental object, according to some embodiments of the disclosure.

In some embodiments, displayed feedback indicates an insufficiency of measurement data, for example, for a region of the dental object being measured. FIG. 8E is a simplified schematic of a dental measurement device 802 including a feedback display 818 measuring a dental object 810, according to some embodiments of the disclosure. FIG. 8E shows an alternative to FIG. 8D where the scan performed lacks data for a portion of the dental object as indicated by unilluminated light 818a.

FIGS. 9A-B are a simplified schematic of a dental measurement device 902 including a feedback display 918 measuring a dental object 910, according to some embodiments of the disclosure.

In some embodiments, FIGS. 9A-B illustrate display of feedback on dental measurement device 902 based on an orientation of the device with respect to the dental object 910 being measured. FIGS. 9A-B illustrate orientation of information displayed on feedback display 818 remaining constant with respect to an orientation of dental object 910 when an orientation of the dental device changes from FIG. 9A to FIG. 9B.

Exemplary Display Selection According to Some Embodiments

Figure 10:
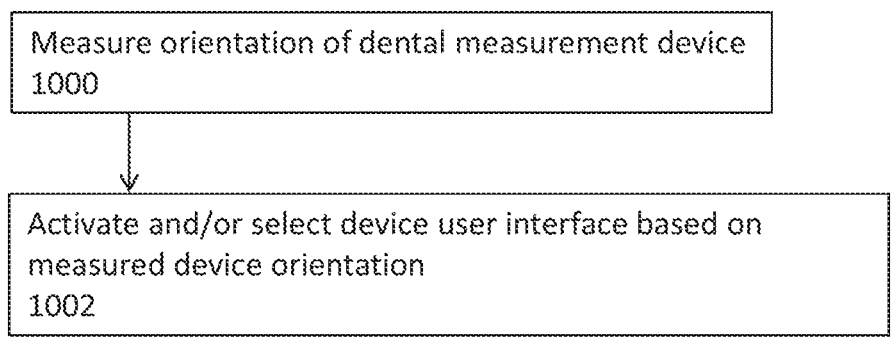
FIG. 10 is a flow chart for a method of selecting a user interface, for a dental measurement device, according to some embodiments of the disclosure.

FIG. 10 is a flow chart for a method of selecting a user interface, for a dental measurement device, according to some embodiments of the disclosure.

At 1000, in some embodiments, an orientation of a dental measurement device is measured.

At 1002, in some embodiments, a user interface is selected and/or activated for display of information based on measured orientation of the dental measurement device. For example, without using measurement as to a position and/or line of sight of a user, where, for example, in some embodiments, user position is inferred from the orientation of the dental measurement device.

Optionally, in some embodiments, a user's line of sight is estimated, for example, with respect to the dental measurement device and/or dental object being measured and visual user interface/s are selected and/or activated for display of information based on measured orientation of the dental measurement device with respect to a user's line of sight. In some embodiments, a user interface which is most visible to a user is selected.

In some embodiments, an audio and/or haptic user interface is selected based on orientation of the dental measurement device with respect to a user. For example, where, in some embodiments, position of a user's hand is inferred from an orientation of the device and/or an orientation of the device with respect to the user, the position of the user's hand then, in some embodiments, being used to select a haptic user interface. For example, where, in some embodiments, an audio user interface is selected based on an orientation of the dental measurement device with respect to a user, e.g. based on user ear position e.g. estimated from collected image/s.

Figure 11A:
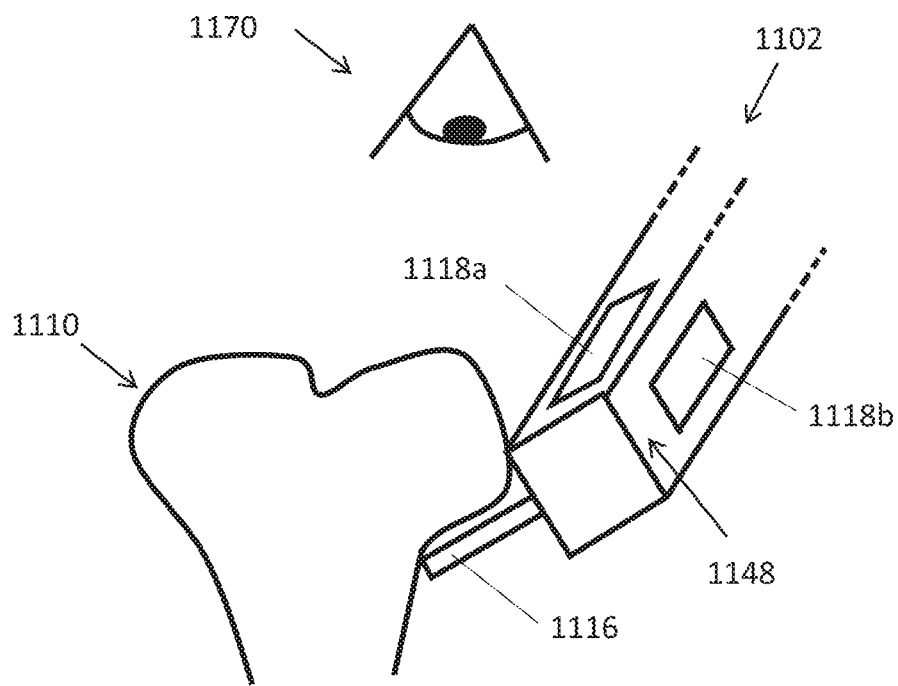
FIG. 11A is a simplified schematic of a distal portion of a dental measurement device measuring a dental object, according to some embodiments of the disclosure.

FIG. 11A is a simplified schematic of a distal portion of a dental measurement device 1102 measuring a dental object 1110, according to some embodiments of the disclosure.

In some embodiments, a dental measurement device is orientated such that a user interface display 1118b is at least partially obscured from a user's line of sight 1170.

For example, as described and/or illustrated in FIG. 3, in some embodiments dental measurement device 1102 is tilted such that a top surface 1128 of a body of the dental measurement device (top surface 1128 e.g. opposing a surface from which a stylus protrudes 1116) is at least partially obscured from user view 1170.

In some embodiments, information (e.g. feedback e.g. images collected by the dental measurement device cameras) displayed on display 1118*b* is distorted and/or changed based on visibility of the display to the user. For example, in some embodiments, feedback displayed on (e.g. only on) a portion of display 1118*b* visible to the user (e.g. an upper portion of display 1118*b* in the orientation illustrated in FIG. 11A).

Additionally or alternatively, in some embodiments, e.g. as the dental measurement device is moved, partially and/or fully obscured display/s (e.g. display 1118*b* in the orientation illustrated in FIG. 11A) are deactivated and/or an unobscured display/s are activated 1118*a*. Where "activation", in some embodiments, refers to display of information by the display.

Exemplary Display of Obscured View/s According to Some Embodiments

In some embodiments, one or more of a user's view of; a portion of a patient's mouth being measured, a portion of a dental measurement device, a dental measurement device display, is obscured by an obstruction.

In some embodiments, the obstruction is one or more of; a portion of the dental measurement device itself, a portion of the patient's mouth, a portion of a user (e.g. the user's hand), and another dental device (e.g. disposed within the mouth e.g. a suction device).

Returning now to FIG. 11A, in some embodiments, a view of a stylus 1116 of dental measurement device 1102 is obstructed by dental object, e.g. the dental object 1110 being measured.

In some embodiments, a portion of a patient's mouth and/or a portion of a dental measurement device which is obscured from a line of sight of a user (e.g. dentist) is displayed by a display visible to the user.

Figure 11B:
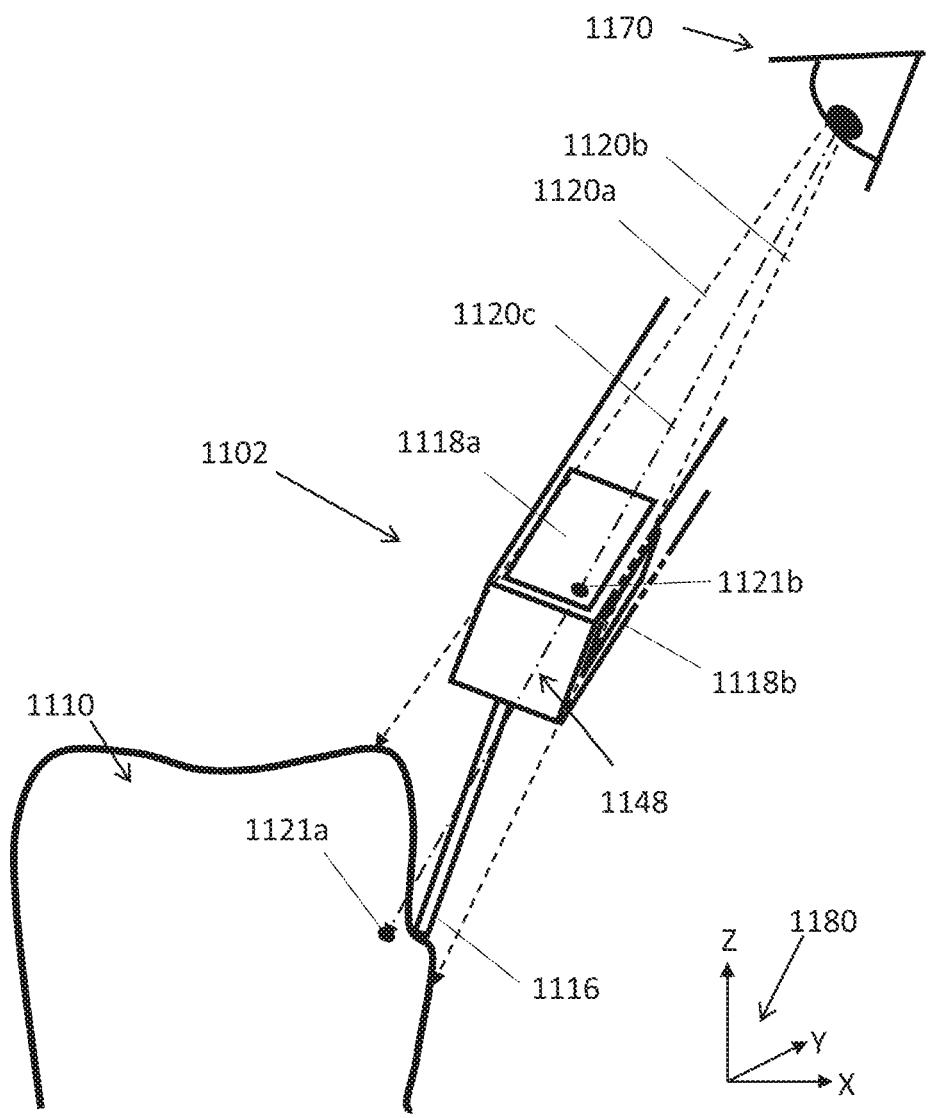
FIG. 11B is a simplified schematic of a distal portion of a dental measurement device measuring a dental object, according to some embodiments of the disclosure.

FIG. 11B is a simplified schematic of a distal portion of a dental measurement device 1102 measuring a dental object 1110, according to some embodiments of the disclosure.

In some embodiments, dental measurement device 1102 is orientated such that the dental measurement device at least partially obscures a dental object 1110 being measured from a user's line of sight 1170. In FIG. 11B, an area of tooth 1110 obscured from user's line of sight 1170 is a tooth area between schematic dashed lines 1120*a* and 1120*b*.

Figure 12A:
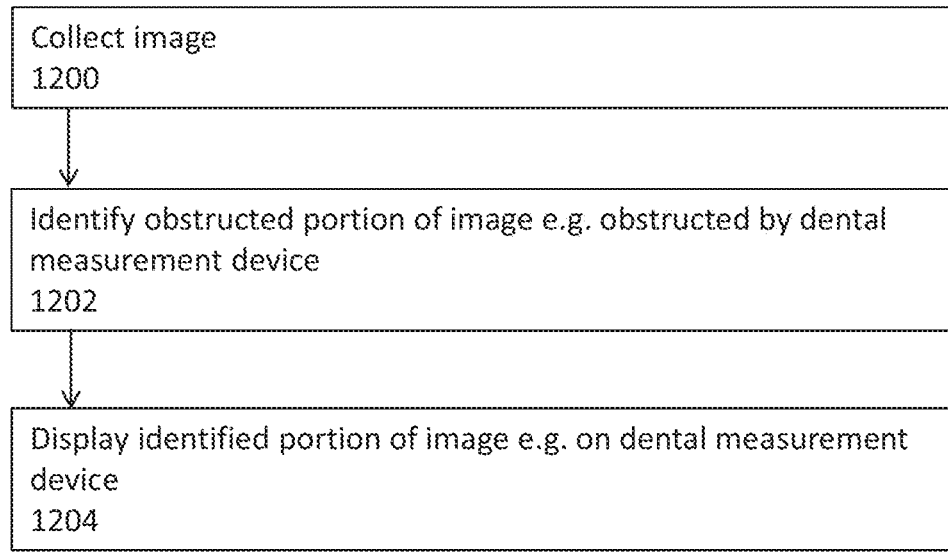
FIG. 12A is a flow chart of a method of display of an obstructed portion of a patient mouth, according to some embodiments of the disclosure.

FIG. 12A is a flow chart of a method of display of an obstructed portion of a patient mouth, according to some embodiments of the disclosure.

At 1200, in some embodiments, an optical image is collected, for example, by one or more optical sensor (e.g. camera) of a dental measurement device.

Optionally, at 1202, in some embodiments, images undergo image processing. For example, in some embodiments, information is overlaid onto optical image/s. For example, in an exemplary embodiment, a portion of the optical image corresponding to obstructed object/s (e.g. portion/s of the patient's mouth and/or dental measurement device), is identified.

At 1204, in some embodiments, the collected optical image/s e.g. the identified portion of the optical image, are displayed, for example, on a display located on the dental measurement device.

Figure 12B:
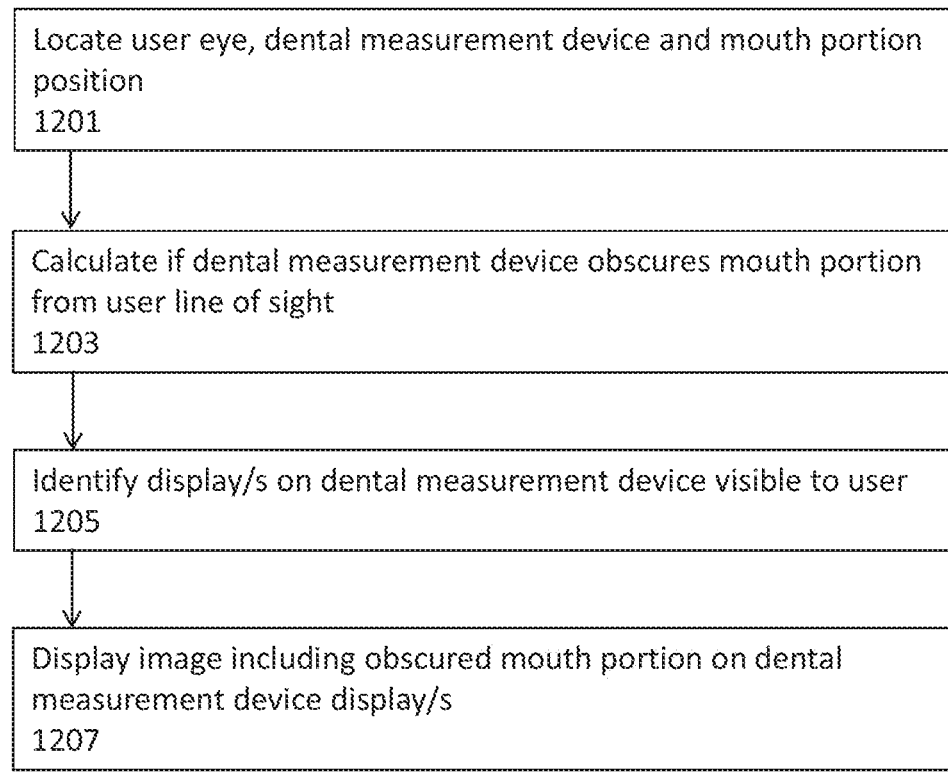
FIG. 12B is a flow chart of a method of display of obstructed views of the mouth, according to some embodiments of the disclosure.

FIG. 12B is a flow chart of a method of display of obstructed views of the mouth, according to some embodiments of the disclosure.

At 1201, in some embodiments, positions of a user's eye/s, a dental measurement device and a mouth portion being measured are measured. For example, using one or more camera and/or position sensor. For example, in some embodiments, positions are estimated using collected images by one or more camera located on the dental measurement device and/or known dimensions of the dental measurement device.

For example, in some embodiments, images collected by the dental measurement device are used to generate a 3D model of a mouth portion (e.g. including one or more teeth) where the model has a coordinate system (e.g. coordinate system 1180 FIG. 11B). In some embodiments, position of the dental measurement device is also known within the 3D model coordinate system, e.g. using known information regarding the dental measurement device camera (e.g. position within the dental measurement device) and/or known dimension/s of the dental measurement device. In some embodiments, a user eye location is found in the coordinate system, for example, using images collected, by additional camera/s (optionally part of the dental measurement device). Where, for example, a co-ordinate system of a first data set (e.g. collected by a first camera e.g. including images of mouth portions) is aligned with a co-ordinate system of a second data set (e.g. collected by a second camera e.g. including images of the user's eyes).

At 1203, in some embodiments, whether the dental measurement device obscures mouth portion/s being measured from a user's line of sight and/or what mouth portion/s are obscured is calculated. For example, using on estimated position of user's eye/s and/or position of the dental measurement device and/or position of mouth portions being measured and/or known dimensions of the dental measurement device.

Optionally, at 1205, in some embodiments, display/s on the dental measurement device visible to a user are selected, for example, based on position and/or orientation of the dental measurement device and/or known dimensions of the dental measurement device and/or user eye position.

At 1207, in some embodiments, image/s including obscured portion/s of the patient's mouth are displayed, for example on selected dental measurement device display/s. Alternatively, the images are displayed on an external display (e.g. display 124 FIG. 1, display 224 FIG. 2). In some embodiments, images are processed before display.

FIG. 13A is a simplified schematic of a dental measurement device 1302 displaying an image 1304 of an obscured portion of a patient mouth 1304, according to some embodiments of the disclosure.

FIG. 13B is a simplified schematic of an image collected by a dental measurement device, according to some embodiments of the disclosure. In some embodiments, the image is collected by dental measurement device 1302 of FIG. 13A.

FIG. 13C is a simplified schematic of an obscured portion of the image of FIG. 13A, according to some embodiments of the disclosure. In some embodiments, the obscured portion is the portion of the patient mouth obscured by dental measurement device 1302 of FIG. 13A.

In some embodiments, the obscured portion of the image (e.g. illustrated by FIG. 13C) is generated from the collected image (e.g. illustrated by FIG. 13B).

In some embodiments, collected image/s and/or obscured portion/s of image/s include at least a portion of a dental measurement device stylus 1316. In some embodiments, obscured portion 1304 is displayed on a display mounted on dental measurement device 1302.

In some embodiments, collected image/s (e.g. as illustrated by FIG. 13B) are processed (e.g. cropped) so that when the image is displayed on display 1318 the image is aligned with a user's view of unobscured portion/s of the patient/s mouth 1310 and/or dental measurement device.

For example, referring back to FIG. 11B, known geometry of dental measurement device 1148, position of user's eyes 1170 and position of dental object 1110 (e.g. in a coordinate system, e.g. as described regarding step 1201 FIG. 12B) are used to process collected images before display on display 1118a, such that the displayed image is aligned with the real tooth image. For example, in some embodiments, obscured point 1121a is shown on display 1118a as point 1121b. Where, e.g. using models of the tooth portion and dental measurement device and user's eye position within a coordinate system, the point 1121b is obtained as the intersection between a plane of display 1118a with a ray 1120c connecting a user eye 1170 tooth point 1121a.

Figure 14:
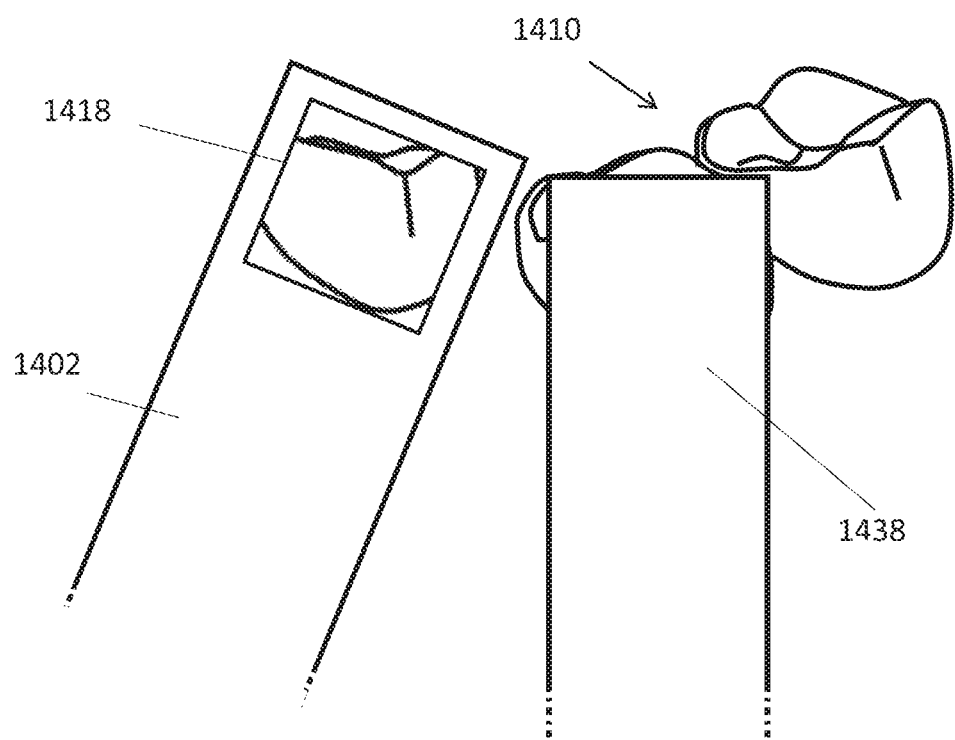
FIG. 14 is a simplified schematic of a dental measurement device including a display of an obscured mouth portion, according to some embodiments of the disclosure.

FIG. 14 is a simplified schematic of a dental measurement device 1402 including a display of an obscured mouth portion, according to some embodiments of the disclosure.

In some embodiments, an additional device and/or an object (e.g. portion of a user's hand) 1438 (e.g. a suction tool, a drill) obscures a portion of a patient's mouth being measured. In some embodiments, image/s collected by dental measurement device 1402 (e.g. by camera/s of the dental measurement device) are processed to generate an image of a mouth portion which is obscured from a user's line of sight by the additional device. In some embodiments, processing of image/s is based on position of the additional device and/or dental measurement device and/or mouth portion 1410 and/or user's eyes within a co-ordinate space. In some embodiments, the image of the obscured mouth portion is displayed on a dental measurement device display 1418.

Figure 21:
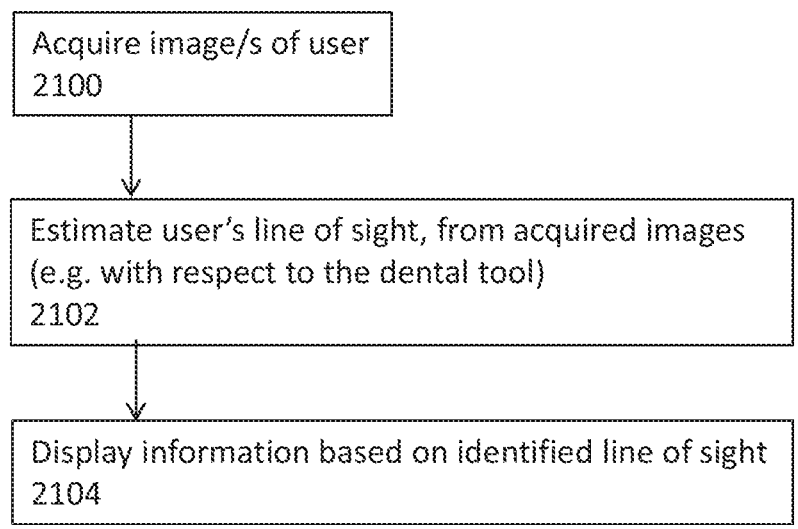
FIG. 21 is a flow chart of a method of display, according to some embodiments of the disclosure.

Exemplary Display Based on Spatial Relationship Between User and Dental Measurement Device According to Some Embodiments FIG. 21 is a flow chart of a method of display, according to some embodiments of the disclosure.

At 2100, in some embodiments, one or more image is collected of a user. For example, using one or more camera on the dental measurement device. Alternatively or additionally, using one or more camera external to the measurement device (e.g. on a system display and/or mounted in a dental clinic room).

At 2102, in some embodiments, a user's position and/or line of sight (for example, of the user's eye/s e.g. 1170 FIG. 11B) 1170 is estimated from image/s collected (e.g. by image processing module 514 FIG. 5). Where the position of the user is, in some embodiments, with respect to the dental measurement tool. Optionally, additional information is used in the estimation, for example, measurement from one or more other dental tool sensor (e.g. orientation information measured by sensor/s e.g. position sensor/s 502 FIG. 5). In some embodiments, user facial feature/s (e.g. eye position) are extracted from collected images to provide an estimation of user line of sight. For example, using one or more face detection technique and/or eye gaze direction detection technique. In some embodiments, user position and/or line of sight is estimated without using image/s e.g. using other sensor data.

At 2004, in some embodiments, information is displayed on and/or by the dental measurement tool, based on the identified line of sight and/or position of the user with respect to the dental tool.

For example, in some embodiments, one or more display is selected e.g. one or more visual display and/or one or more audio display is selected based on the line of sight and/or position. For example, in some embodiments, one or more display is adjusted e.g. an orientation of information displayed on visual display/s e.g. one or more audio feature of an audio display e.g. volume e.g. increasing the volume with distance of the tool from the user.

Exemplary Dental Measurement Device According to Some Embodiments

Figure 15A:
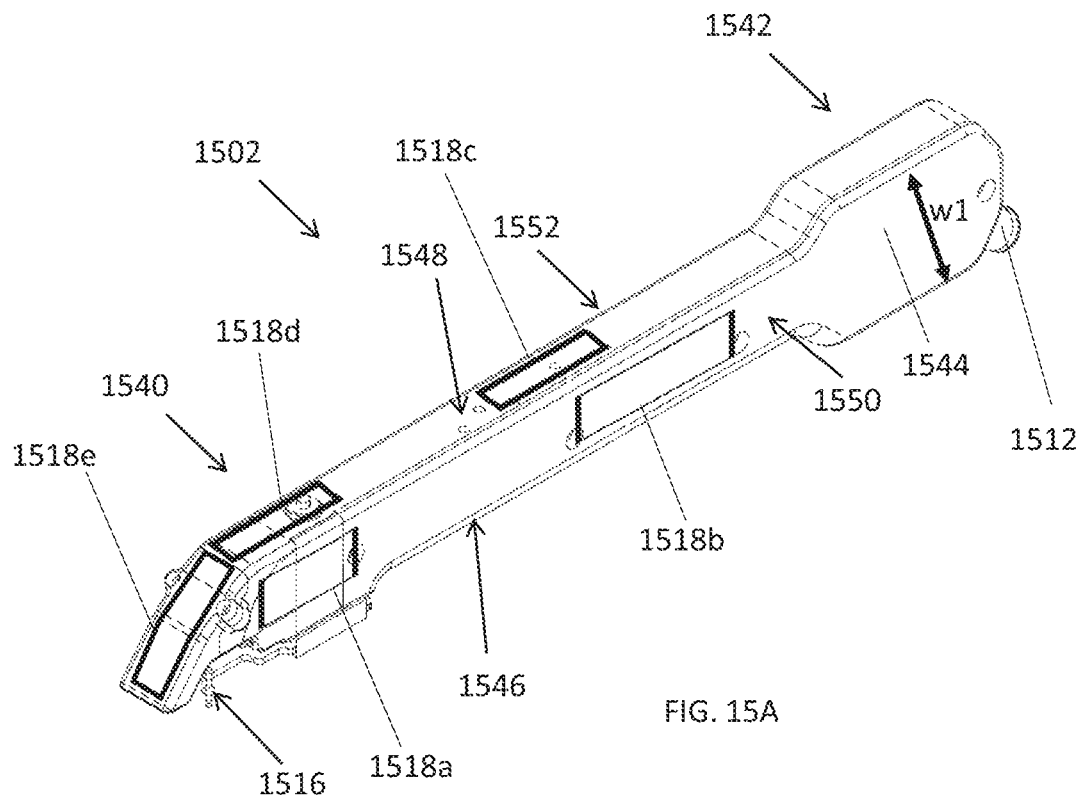
FIG. 15A is a simplified schematic of an exemplary dental measurement device, according to some embodiments of the disclosure.

FIG. 15A is a simplified schematic of an exemplary dental measurement device 1502, according to some embodiments of the disclosure.

Figure 15B:
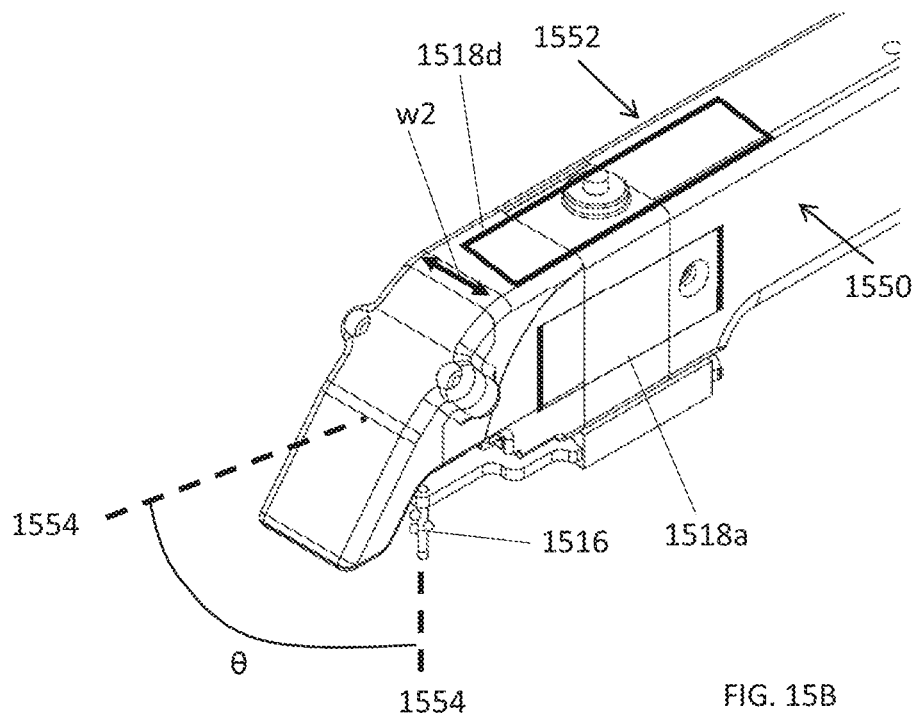
FIG. 15B is a simplified schematic of a distal portion of the exemplary dental measurement device of FIG. 15A, according to some embodiments of the disclosure.

FIG. 15B is a simplified schematic of a distal portion 1540 of the exemplary dental measurement device of FIG. 15A, according to some embodiments of the disclosure.

Figure 15C:
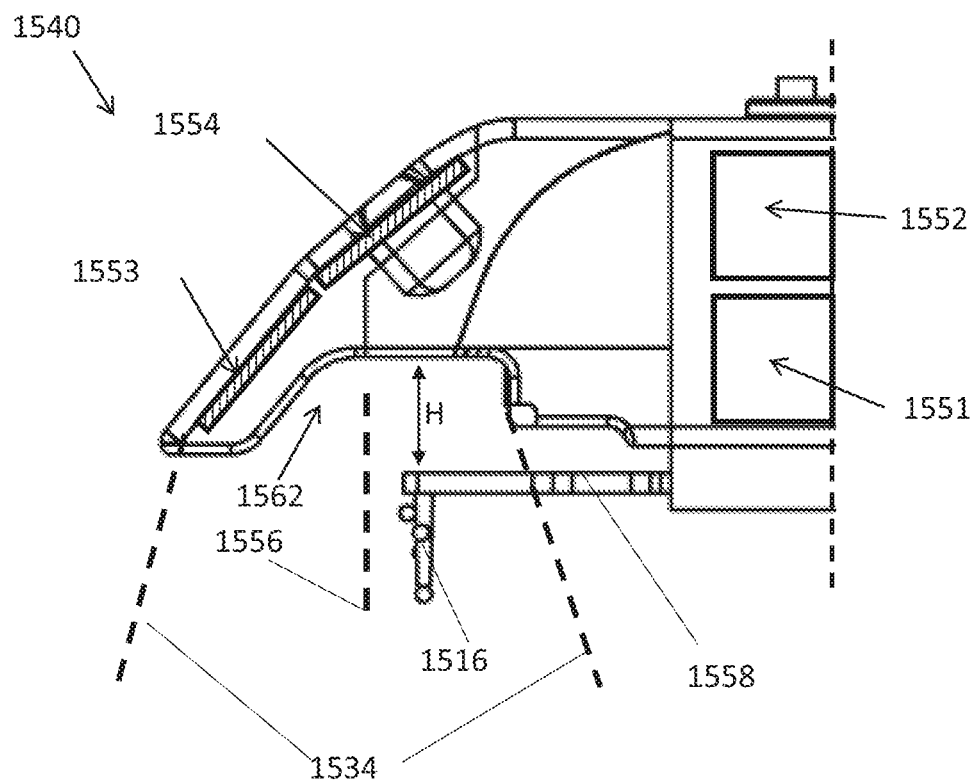
FIG. 15C is a simplified schematic section of a distal portion of an exemplary dental measurement device, according to some embodiments of the disclosure.

FIG. 15C is a simplified schematic section of a distal portion 1540 of an exemplary dental measurement device 1502, according to some embodiments of the disclosure.

Figure 15D:
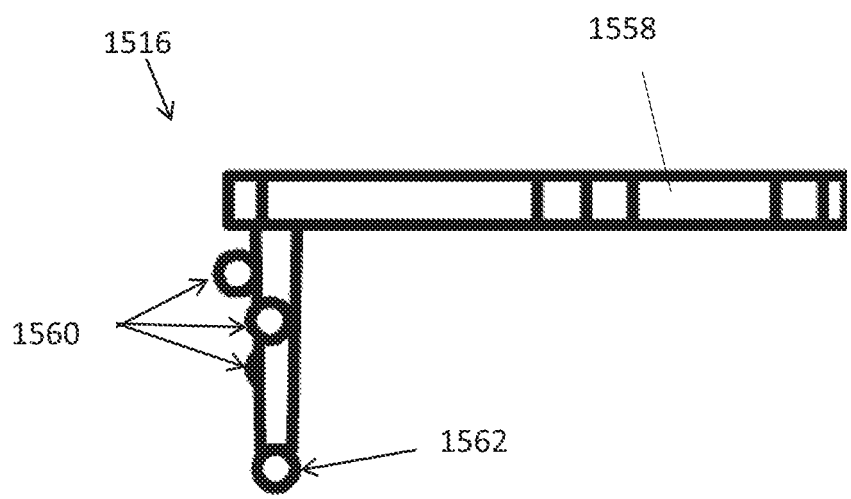
FIG. 15D is a simplified schematic side view of a stylus of a dental measurement device, according to some embodiments, of the disclosure.

FIG. 15D is a simplified schematic side view of a stylus 1516 of a dental measurement device, according to some embodiments, of the disclosure.

In some embodiments, dental measurement device 1502 is an elongate shape including a distal portion 1540 configured to be inserted into a patient's mouth for measurements and a proximal end 1542. In some embodiments, distal portion 1540 is sized and/or shaped for insertion into a patient's mouth. Referring to FIG. 15B, in some embodiments, a width, w2 of dental measurement device 1502, at least at a distal portion of the device is less than 10 mm or less than 5 mm or 1-20 mm, or 1-15 mm, or 2-12 mm, or 3-8 mm or 5-10 mm, about 5 mm, or about 10 mm, or lower or higher or intermediate ranges or widths. Where a distal portion of the device is the most distal 0.5-10 cm, or 1-5 cm or lower or higher or intermediate lengths or ranges or the most distal 1-50%, or 1-20%, or lower or higher or intermediate ranges or percentages of a long axis length of the device.

In some embodiments, dental measurement device includes a stylus 1516. In some embodiments, stylus 1516 extends away from a body of dental measurement device 1502 at an angle. In some embodiments, e.g. as illustrated in FIGS. 15A-B stylus 1516 extends at an angle θ from a central long axis 1554 of dental measurement device. In some embodiments, θ is about 90°, or 20-150°, or 45-135°, or 80-100° or lower or higher or intermediate ranges or angles.

In some embodiments, dental measurement device 1502 includes one or more optical sensor.

Referring now to FIG. 15D, in some embodiments, the dental measurement device includes one or more optical element, where, in some embodiments, one or more optical element transfers an optical signal towards optical sensor/s. In some embodiments, one or more optical element transfers illumination from a light source within the device and/or out of the dental measurement device.

In an exemplary embodiment, the dental measurement device includes a first mirror 1553 which transfers light towards a camera lens 1551 and a second mirror 1554 which transfers light emanating from a projector lens 1552 out of the dental measurement device. In some embodiments, the dental measurement device is configured to illuminate a mouth portion with structured light. Alternatively, in some embodiments, the dental measurement device lacks a projector and/or light source and/or a single mirror is used to transfer light in and out of the dental measurement device (e.g. 1553 and 1554 being joined into a single mirror which, in some embodiments, is curved).

In some embodiments, a FOV 1534 of the optical sensor includes at least a portion of stylus 1516. In some embodiments, a central axis 1556 of FOV 1534 is at an angle to central long axis 1554 of the dental measurement device where the angle, in some embodiments, is about 90°, or 20-150°, or 45-135°, or 80-100° or lower or higher or intermediate ranges or angles.

Referring back not to FIG. 15A, in some embodiments, dental measurement device includes a housing which includes an underside 1546, a top side 1548, and two lateral sides 1550, 1552. In some embodiments, the top side and the underside are generally opposite each other and, in some embodiments, are parallel to each other. In some embodiments, the lateral sides are generally opposite each and, in some embodiments, are parallel to each other. In some embodiments, cross sections of dental measurement device housing taken perpendicular to a central long axis of the housing are generally rectangular.

In some embodiments, dental measurement device includes a different shape, for example, including one or more cylindrical portion.

In some embodiments, dental measurements are collected at distal end 1540 of measurement device 1502. In an exemplary embodiment, optical data is collected. In some embodiments, optical data is directly collected by one or more optical sensor (e.g. camera) located at a distal portion 1540. Additionally or alternatively, in some embodiments, images are reflected towards a sensor within a body of measurement device.

In some embodiments, proximal end 1542 of dental measurement device 1502 includes a handle 1544 portion which is grasped by a user during measurement with the device. In some embodiments handle 1544 is sized and/or shaped to be comfortably grasped by an adult user's hand e.g. referring to FIG. 15A where a width, w1 of the handle is 5-30 mm, or 10-20 mm, or lower or higher or intermediate ranges or widths.

In some embodiments, handle 1544 lacks user interface displays. In some embodiments, touch user interface/s (e.g. button, switch, vibrating user interface) are located on and/or near handle 1544 potentially enabling use thereof by a user grasping the device handle.

Alternatively, in some embodiments, handle 1544 includes one or more display, located on one or more side of the handle, where, for example, a user opens their hand (e.g. while supporting the device on their palm) to view a display on the handle.

In some embodiments, dental measurement device 1502 includes one or more connector 1512 for data and/or electrical power connection.

In some embodiments, dental measurement device 1502 includes one or more user interface located on or more side of the device. For example, in some embodiments dental measurement device 1502 includes one or more user interface on a lateral side of the device 1518a, 1518b, and/or one or more user interface 1518c, 1518d located on top side 1548 of the device.

In some embodiments, one or more user interface 1518a, 1518d, 1518e are located at distal portion 1540 of the device, for example, to display information which assists the dentist in positioning of the distal portion 1540 and/or stylus 1516 during measurement (e.g. as described regarding and/or illustrated in FIG. 3).

In some embodiments, dental device 2102 includes one or more user interface, e.g. display screen/s, on underside 1546 of dental device. In some embodiments, user interface/s on underside 1546 (and/or extending onto underside 1546) are used when the user holds dental device 1502 upside down, for example when measuring an upper jaw of a patient.

In some embodiments, user interfaces 1518a-e include one or more of a LCD display, a touch and/or flexible screen, a display including one or more light (e.g. LED, OLED). In some embodiments one or more of user interfaces 1518a-e include one or more touch screen, which, in some embodiments, may be controlled by a user wearing gloves.

Figure 22:
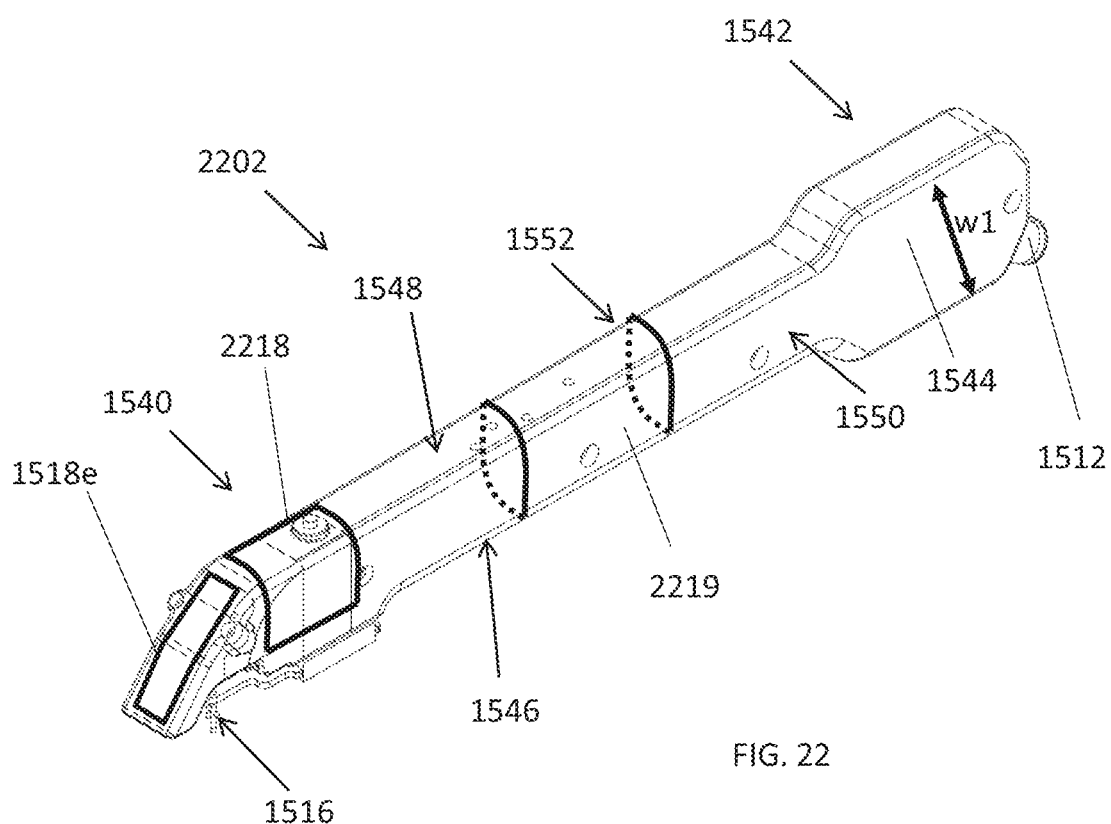
FIG. 22 is a simplified schematic of an exemplary dental measurement device, according to some embodiments of the disclosure.

FIG. 22 is a simplified schematic of an exemplary dental measurement device 2202, according to some embodiments of the disclosure. In some embodiments, dental measurement device 2202 includes one or more feature as described and/or illustrated regarding dental measurement device 1502 FIG. 15.

In some embodiments, dental device 2202 (e.g. a dental measurement device, a dental tool) includes one or more display which extends to cover more than one side of the device e.g. one or more of displays 2218, 2219. For example, two sides, or three sides, or all longitudinal sides (e.g. is wrapped around), or all transverse sides, or forms a sheath extending along at least a portion of the device.

In some embodiments, dental device 2202 includes one or more flexible display, e.g. one or more a flexible display screen 2218, 2219 e.g. flexible LCD display. In some embodiments, the flexible display is mounted on a non-planar topography of the dental device. For example, in some embodiments, a flexible display is wrapped around a portion of the dental device, e.g. covering more than one side of the device e.g. display 2218 which is mounted on two longitudinal sides of dental device 2202 e.g. display 2219 which is extends around a longitudinal portion of dental device 2202.

For example, in some embodiments, a flexible display is mounted on at least a portion of the dental device (e.g. of a housing of the dental measurement device) which includes a convex and/or concave portion and/or a protrusion and/or indentation.

In some embodiments, the dental measurement device includes a display perpendicular (or orientated 30-90°, or 45-90°, or 70-90°, or 80-90°, or about 90°, or lower or higher or intermediate angles or ranges) to a central axis of a field of view (FOV) of the imager of the dental measurement device, for example, on a top surface of the dental measurement device. In some embodiments, the dental measurement device includes a display parallel (or orientated 0-60°, or 0-45°, or 0-20°, or 0-10° or about 0° or lower or higher or intermediate ranges or angles) to the central axis of the FOV, for example, on a side surface of the dental measurement device.

In some embodiments, housing of the dental measurement device is sized and/or shaped to enable visibility of stylus 1516 to the user during collection of measurements. For example, visibility of stylus potentially enables the user to more accurately position the stylus e.g. inserting and/or moving the stylus between a tooth surface and surrounding gums without damaging the gums and/or while damaging the gums a minimally.

In some embodiments, a housing of the dental device has an inlet 1562 above the stylus, potentially increasing the visibility of stylus 1516, e.g. from the side, e.g. when the dental device is tilted.

In some embodiments, stylus 1516 is attached, by connector 1558, to dental measurement device 1502 at a point outside FOV 1534 of optical sensor/s 1516 potentially reducing obstruction of optical sensor views of the patient's mouth, associated with the stylus.

In some embodiments, stylus 1516 includes one or more marker 1560 (e.g. as described in U.S. Pat. No. 9,454,846).

In some embodiments, stylus 1516 includes a rounded tip 1562.

In some embodiments, stylus 1516 is removably attached to the dental measurement device. In some embodiments, stylus 1516 is autoclavable, for example, constructed of stainless steel. In some embodiments, stylus 1516 and connector 1558 are one piece which is removably attached to the dental measurement device.

In some embodiments, the dental measurement device includes a display perpendicular (or orientated 30-90°, or 45-90°, or 70-90°, or 80-90°, or about 90°, or lower or higher or intermediate angles or ranges) to a central long axis of a dental measurement device stylus, for example, on a top surface of the dental measurement device. In some embodiments, the dental measurement device includes a display parallel (or orientated 0-60°, or 0-45°, or 0-20°, or 0-10° or about 0° or lower or higher or intermediate ranges or angles) to the central long axis of the stylus, for example, on a side surface of the dental measurement device.

Exemplary System Control According to Some Embodiments

In some embodiments, one or more part of a dental measurement system (e.g. a dental measurement device and/or external display and/or control console) is controlled by a user input at the dental measurement device.

Figure 16:
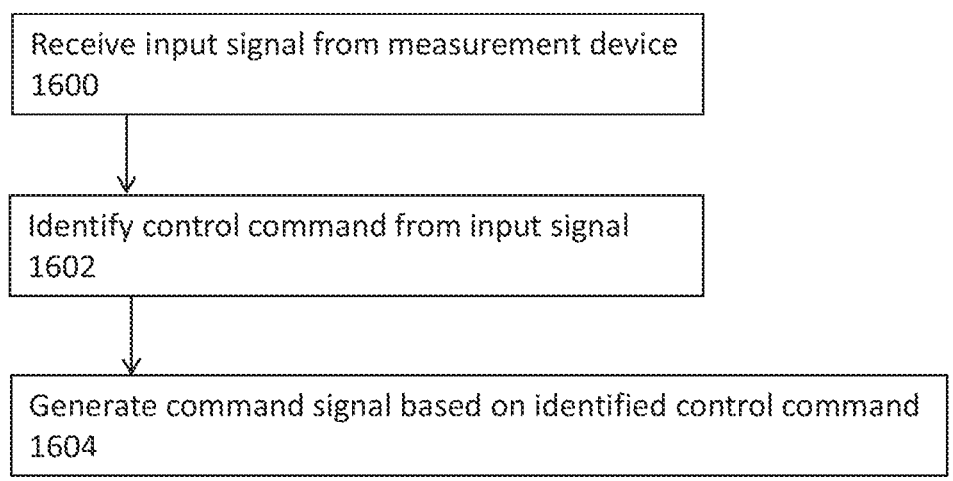
FIG. 16 is a flow chart of a method of control of a dental measurement system, according to some embodiments of the disclosure.

FIG. 16 is a flow chart of a method of control of a dental measurement system, according to some embodiments of the disclosure.

At 1600, in some embodiments, a control signal is received from a dental measurement device.

In some embodiments, the control signal is produced by a user input at a user interface (e.g. located on the dental measurement device), where the user interface is for example, a button, a switch, a touch screen.

In some embodiments, the control signal is received from one or more sensor (e.g. dental measurement device sensor) which, for example, senses a gesture performed by the user and/or other user control input (e.g. a vocal command, e.g. movement and/or change in orientation and/or position of the dental measurement device).

At 1602, in some embodiments, the control signal is identified by a processor.

At 1604, in some embodiments, the processor generates a command signal based on the identified control signal.

In some embodiments, the command signal controls the dental measurement device, for example, initiating a start to collection of measurements with the device.

In some embodiments, the command signal controls another part of the system, for example, an additional device (e.g. in proximity to the dental measurement device) and/or an external display (e.g. display 124, FIG. 1, 224, FIG. 2).

In some embodiments, one or more dental measurement device position and/or orientation sensor (e.g. within an IMU) provides a control signal which controls a display and/or controls the dental measurement system through control of a display.

In some embodiments, the dental measurement system includes a mode where the dental measurement device controls aspect/s of the system through control of a display. For example, in some embodiments, a control signal includes measurement of dental measurement device orientation and/or position and/or movement which controls a display, e.g. an external display (e.g. display 124, FIG. 1, 224, FIG. 2). Where, for example, the display is a user interface, through which a user selects options and/or inputs data, for example, by selecting a region of the display e.g. an option on a menu (e.g. menu 230 FIG. 2).

For example, in some embodiments, position of a cursor on a display is controlled by position and/or movement and/or orientation of the dental measurement device. For example, in some embodiments, a selected region of a display is controlled by position and/or movement and/or orientation of the dental measurement device. In some embodiments, one or more user interface on the dental measurement device (e.g. button and/or rotation wheel) is used to control the display e.g. the dental measurement device generating a control signal upon pressing of the button and/or rotation of the rotation wheel.

In some embodiments, selected option/s control display of information, for example selection and/or deselection of layers of information, e.g. of a 3D model.

In some embodiments, a user selects and/or inputs a tooth number of the tooth or teeth for a planned scan and/or for a completed scan. In some embodiments, the user selects tooth number/s from a graphical representation of a jaw or jaws.

In some embodiments, a user selects and/or inputs material and/or process parameters for producing a dental prosthetic, e.g. where the prosthetic is constructed using a generated 3D model.

In some embodiments, selected option/s control operation of the dental measurement device (e.g. measurements e.g. initiating of measurements) and/or other portion/s of the dental measurement system (e.g. additional device/s).

FIG. 17 is a simplified block diagram of a control infrastructure for a dental measurement system, according to some embodiments of the disclosure.

In some embodiments, the system includes one or more sensor, for example sensors 1704, 1720, 1702, 1718, 1722. In some embodiments, one or more of sensors 1704, 1720, 1702, 1718, 1722 are located on a dental measurement device. In some embodiments, one or more of the sensors sense user interaction with the dental measurement device.

In some embodiments, optical sensor/s 1704, include one or more optical sensor (e.g. one or more camera) within the dental measurement device (e.g. camera 106 FIG. 1, optical sensor 206 FIG. 2).

In some embodiments, sound sensor/s 1720 include one or more microphone, e.g. on and/or within the dental measurement device e.g. 222 FIG. 2.

In some embodiments, position sensor/s 1702 (e.g. located on and/or within the dental measurement device) include one or more IMU and/or gyroscope and/or one or more accelerometer. Additionally or alternatively, in some embodiments, position sensor/s 502 include one or more electromagnetic position sensor and/or one or more ultrasonic position sensor.

In some embodiments, optical sensor/s act as position sensor/s, for example, in some embodiments, an image processing module 1726 identifies position of the dental measurement device from optical images which, in some embodiments, are collected by the device. For example, by identifying marker/s (e.g. at known locations) within images. For example, by comparing images with previously collected measurement/s (e.g. measurement model/s).

In some embodiments, imaging processing module 1726 identifies position of the dental measurement device with respect to object/s, for example, marker/s and/or dental object/s and/or a user (e.g. a portion of a user, e.g. a user's face, where the object/s are identified from image/s collected by imager optical sensor/s).

In some embodiments, imaging processing module 1726 identifies user eye position, for example, in successive images, to track user eye movement/s. Where the user's eye position, is identified with respect to the dental measurement device and/or one or more other object (e.g. dental object e.g. dental tool). For example, to provide a user's line of sight e.g. with respect to the dental measurement device and/or one or more other object.

In some embodiments, contact sensor/s 1718 include one or more strain gauge mounted on the dental measurement device (e.g. as described in U.S. Pat. No. 9,454,846).

In some embodiments, proximity sensor/s include one or more RFID reader and/or electromagnetic sensor and/or ultrasonic sensor. In some embodiments, the dental measurement device includes a sensor e.g. RFID reader, electromagnetic sensor. Alternatively or additionally, in some embodiments, the dental measurement device includes a tracked element, for example, a magnet (e.g. an electromagnet) and/or a RFID tag.

In some embodiments, one or more of the sensors sends a signal to a processing application 1706. In some embodiments, processing application 1706 is hosted by a processer located in the dental measurement device, alternatively or additionally, in some embodiments, processing application 1706 is hosted externally to the dental measurement device, e.g. at a control console.

In some embodiments, processing application 1706 hosts one or more recognition module 1724, 1725, 1726, 1728, 1730.

In some embodiments, processing application 1706 includes a voice recognition module 1724 which is configured to identify vocal commands from a user as sensed by one or more sound sensor 1720. For example, in some embodiments, a user vocally commands a start or stop to collection of dental measurements with the dental measurement device. In some embodiments, a user vocally commands a change of mode of the device, e.g. from a data collection mode to a model marking mode (e.g. as described regarding FIGS. 19 and/or 20)

In some embodiments, processing application 1706 includes one or more contact recognition module 1728 which is configured to identify contact between the device and other objects using, for example, data received from one or more contact sensor 1718 and/or one or more RFID reader and/or electromagnetic sensor and/or ultrasonic sensor and/or data received from one or more optical sensor 1704 where, in some embodiments, optical sensor/s include camera/s.

For example, in some embodiments, the dental measurement device includes a stylus and contact of the stylus, for example, between the stylus and a portion of a patient's mouth (e.g. a tooth), and may be identified from sensor signal/s.

In some embodiments, one or more strain gauge located, for example, on the stylus and/or at a connection between the stylus and the dental measurement device provides a signal to contact recognition module 1728.

Additionally or alternatively, in some embodiments, contact of the stylus is identified from images collected by optical sensor/s, for example, by image processing software e.g. within contact recognition module 1728. In some embodiments, contact recognition module identifies, from collected images, contact from a measured deflection of the stylus (deflection e.g. measured by movement of one or more marker on the stylus e.g. markers 1560 FIG. 15D). For example, where contact is identified at over a threshold deflection. For example, where contact suitable for collection of dental measurements In some embodiments, contact is identified (e.g. by image processing software) optically by a "jump" in the image and/or other characteristic changes to collected images when contact is made (e.g. between the stylus and a patient mouth portion).

In some embodiments, measured deflection of the stylus provides measurement of force of contact between the stylus and another object (e.g. a dental object).

In some embodiments, contact recognition module 1728 identifies a desired level of contact (e.g. force of contact, e.g. contact between the stylus and a dental object) for collection of measurement (e.g. of the object) using the stylus. For example, in some embodiments, desired contact is over a threshold force and/or under a threshold force (e.g. as measured, in some embodiments, by stylus deflection). For example, in some embodiments, desired contact is within a range of measured forces (e.g. as measured, in some embodiments, by stylus deflection).

In some embodiments, upon identifying too high contact force (and/or stylus deflection) or too low contact force (and/or stylus deflection) (e.g. lack of contact), the system displays feedback to the user. For example, where, in some embodiment, upon identifying contact recognition module 1728 sends a signal to command generation module 1732 which sends a signal to one or more user interface 1742. In some embodiments, different feedback is used for low or lack of contact than for too high contact force. For example, lack of contact being displayed visually e.g. by a light and too high contact force (and/or stylus deflection) being displayed audibly e.g. by an alarm. In some embodiments, processing application 1706 includes a proximity detection module 1730, configured to identify proximity of the dental measurement device to one or more additional object. For example, in some embodiments, one or more proximity sensor 1722 measures a proximity of the dental measurement device to another device (e.g. suction device) and, in some embodiments, proximity detection module 1730 sends a signal to command generation module, for example, upon the detected proximity being above a threshold.

In some embodiments, proximity between the dental measurement device and another device is measured using images collected by optical sensor/s 1704. Alternatively or additionally, proximity sensor/s e.g. measure proximity.

In some embodiments, proximity detection module 1730 accesses stored data (e.g. from a database, not illustrated in FIG. 17). In some embodiments, the stored data includes previously collected measurement data. Where, for example, measured mouth portion/s are associated with other data. For example, in some embodiments, stored data includes a region and/or point labeled as requiring more measurement and/or as being a last measurement point (e.g. where measurement ceased) and/or as being an edge to a measurement region. In some embodiments, proximity detection module 1730 identifies a proximity between a dental measurement device and a labeled mouth portion, e.g. using collected images and sends the identified proximity to command generation module 1732. In some embodiments, command generation module automatically commands a start of measurement, e.g. when a threshold proximity is detected. For example, the measurement device automatically resuming measurements when the device is in close enough proximity to a labeled area. For example, in an exemplary embodiment, measurement resumes when a user positions the dental measurement device at a region where measurements were paused. In some embodiments, command generation module displays an indication to a user of proximity to a labeled region and/or point.

In some embodiments, position sensor/s 1702 send a signal to command generation module, where for example, an orientation of the dental measurement device, optionally with respect to another object (e.g. a dental object, e.g. another system component) initiates a system command. For example, in an exemplary embodiment, a particular orientation of a dental measurement device with respect to an additional device activates the device e.g. when the dental measurement device is orientated such that a stylus of the dental measurement device extends towards the additional device. In some embodiments, an orientation of one or more display of the dental measurement device is measured.

In some embodiments, processing application 1706 includes a gesture recognition module 1725 which receives sensor data and/or data from recognition module data and, based on the received data, sends different signals to command generation module 1732. In some embodiments, gesture recognition module 1725 is configured to identify command gestures initiated by a user from sensor data and/or recognition module data.

In some embodiments, the gesture recognition module is configured to identify (e.g. from position sensor data and/or optical sensor data and/or data from one or more additional sensor) one or more movement gesture. Where, in some embodiments, a movement gesture includes moving and/or orientating a measurement device, e.g. with respect to one or more object e.g. in a pre-determined fashion. In some embodiments, a movement gesture includes moving and/or orientating a stylus of a measurement device, e.g. with respect to one or more object e.g. in a pre-determined fashion. For example, in some embodiments, the stylus is used as a pointer.

In some embodiments, a movement gesture is with respect to another object, for example, a dental object, the oral cavity, an additional device, marking/s. In some embodiments, a movement gesture is with respect to an additional device (e.g. a mirror or suction tube) where, for example, a gestures include contact with the additional device and/or, tapping of the additional device and/or setting a known spatial relation between the dental measurement device and the additional device (e.g. contacting and/or crossing handles of the dental measurement device and the additional device handles).

For example, in some embodiments, moving the dental measurement device towards an additional device results in change in function (e.g. activation) of the device. For example, in some embodiments, orientating a stylus of the device towards an additional device (e.g. pointing at the additional device with the stylus) results in change in function (e.g. activation) of the device.

In some embodiments, the gesture recognition module is configured to identify gestures from tracked user face position and/or eye position and/or movement (e.g. as identified in image/s e.g. by image processing module 1726).

For example, in some embodiments, a user selects a display by looking at the display. For example, in some embodiments, a user selects displays on a region of a device by looking at the displays e.g. looking at a right side of the dental measurement device selects (and/or activates) display/s located on the right side of the device.

For example, in some embodiments, a user looking at a region of the dental measurement device selects and/or activates and/or modifies function of one or more portion of the device.

In some embodiments, facial movement/s and/or expression/s e.g. blinking e.g. opening and/or closing the user's mouth, are identified from images to provide control signal/s, where, in some embodiments, gesture recognition module identifies gesture/s which are then supplied to command generation module 1732.

In some embodiments, a gesture includes a user looking in a particular direction e.g. with respect to the dental measurement device. For example, in some embodiments, measurements with the dental measurement device are initiated (and/or the device is turned on and/or off) by the user looking at particular region/s of the device e.g. the back side of the device.

In some embodiments, the gesture recognition module is configured to identify one or more contact gesture, where for example, contact gestures include contacting a stylus of the measurement device to a surface (e.g. a tooth surface) at above a threshold pressure and/or for a pre-determined amount of time (e.g. tapping the device e.g. contacting longer than a first threshold length of time and/or shorter than a second threshold length of time) and/or contacting the surface a pre-defined number of times.

In some embodiments, gesture recognition module 1725 performs signal processing on a signal received from one or more sensor and/or one or more recognition module, to identify a gesture.

For example, in some embodiments, a user inputs different control commands by contacting a stylus of the measurement device to an object in different ways, for example, a different numbers of taps of the stylus against an object and/or different pressure and/or duration of the stylus in contact with an object being identified by gesture recognition module 1725 (e.g. using signal processing) as different gestures.

In an exemplary embodiment, a user taps a tooth surface to initiate a start to collection of dental measurements with the device.

In some embodiments, a gesture includes making a movement with the measurement device while it is in contact with a surface e.g. tracing a letter and/or shape on a surface, for example, the gesture being recognized from inputs received from contact recognition module 1728 and position sensor/s 1702.

In some embodiments, gesture recognition module 1725 receives input from one or more sensor and/or one or more recognition module, where, for example, a user control gesture includes one or more type of input.

For example, in some embodiments, a user controls (e.g. initiates a start to measurement using the dental measurement device) the system using both a vocal command (e.g. identified by voice recognition module) and by contacting a stylus of the dental measurement device to a measurement starting point (e.g. identified by contact recognition module 1728). In some embodiments, command generation module 1732 receives a signal from one or more user interface 1742 (e.g. 220, 222, 218, 227, 230, FIG. 2).

In some embodiments, command generation module 1732 receives data from one or more sensor and/or one or more system module and/or one or more user interface 1742 and generates system commands based on the received data.

In some embodiments, command generation module 1732 sends control signals to optical sensor/s 1704, e.g. camera/s within the dental measurement device, for example, initiating a start and/or stop to collection of measurements with the device.

In some embodiments, command generation module 1732 sends control signals to other system components.

For example, in some embodiments, command generation module 1732 sends command/s to one or more light 1736 (e.g. on/off and/or light level and/or light patterning), where, light/s 1736, for example illuminate a region of a patient's mouth being measured. In some embodiments, one or more of lights 1736 are mounted on the dental measurement device. In some embodiments, lights 1736 are configured to illuminate mouth portion/s with structured light.

For example, in some embodiments, command generation module 1732 sends control command/s to one or more actuator 1740, for example, in embodiments where a stylus of the dental measurement device vibrates, in some embodiments control commands control the vibration.

For example, in some embodiments, command generation module 1732 sends control command/s to one or more additional device 1738 (e.g. suction device, e.g. dental drill), for example, sending the signal wirelessly and/or through a control console.

In some embodiments, command generation module 1732 sends commands to a tooth model generation module 1734, for example, initiating generation of a model based on collected optical data (e.g. as described in U.S. Pat. No. 9,454,846). In some embodiments, tooth model generation module 1734 is hosted externally to the dental measurement device, e.g. on a control console.

In some embodiments, command generation module 1732 sends control commands to a user interface 1742, for example, commands to control information displayed on the user interface.

In some embodiments, command generation module 1732 generates automatic control signals where, for example, the command is not initiated by a user input and/or gesture.

For example, in some embodiments, commands are generated based on sensed data. For example, in an exemplary embodiment, an additional device 1738 is activated upon detection of sufficient proximity of the additional device 1738 to the dental measurement device. For example, in some embodiments, a level of illumination provided by lights 1736 is automatically controlled based on optical measurement data received (e.g. from optical sensor/s 1704) by the command generation module.

In some embodiments, command generation module 1732 initiates semi-automatic control signals, for example, upon receiving a user control input, a command is sent by command generation module once sensed data is verified. For example, in some embodiments, a user selects (e.g. through a user interface) a "resume measurement mode" and measurements are resumed (e.g. using optical sensors) once the dental measurement device is in a recognized position (e.g. as identified from collected images).

It is to be understood that, in some embodiments, the block diagrams of FIG. 5 and FIG. 17 are combined, where in some embodiments, a dental measurement system includes one or more component illustrated in FIG. 5 and one or more component of FIG. 17.

Exemplary Control of Model Display According to Some Embodiments

In some embodiments, the dental measurement device is operated in a mode where movement of the device controls display of a model of mouth portion/s. In some embodiments, a display of the model reflects a distance and/or orientation of the dental measurement device with respect to the mouth portions modeled by the model. For example, in some embodiments, as the device is advanced towards a modeled portion of a mouth (optionally, while a button is pressed) a display zooms in on the corresponding portion of the model.

FIG. 18 is a flow chart of a method of control of display of a model, according to some embodiments of the disclosure.

At 1800, in some embodiments, at least a portion of a patient's mouth and a dental measurement device are registered to a coordinate space of a 3D model of at least a portion of the patient's mouth.

For example, by comparing images collected by the dental measurement device with the 3D model to identify corresponding portions of the patient's mouth as measured (e.g. in real time) by the dental measurement device with portions of the 3D model.

For example, by matching measured location of markers and/or fiducials (e.g. in the patient's mouth) to corresponding markers in the 3D model.

In some embodiments, the 3D model is a model generated from previous measurements collected by the dental measurement device. In some embodiments, the 3D model is a model generated from previous measurements collected by a different measurement device, e.g. CT images, MRI images, ultrasound images.

At 1802, in some embodiments, display of the 3D model on a display is controlled by a distance and/or orientation of the dental measurement device from the patient's mouth. Alternatively or additionally, in some embodiments, the dental measurement device is used to add data to the 3D model.

FIG. 19 is a flow chart of a method of adding data to a model of at least a portion of a mouth, using a dental measurement device, according to some embodiments of the disclosure.

At 1900, in some embodiments, at least a portion of a patient's mouth and a dental measurement device (e.g. 102 FIG. 1, 202 FIG. 2, 1502 FIGS. 15A-C) are registered to a coordinate space of a 3D model of at least a portion of the patient's mouth, (e.g. as described regarding step 1800, FIG. 18).

At 1902, in some embodiments, a user selects a "mark model" mode, for example, through a user interface and/or performing a command gesture (e.g. a contact gesture). For example, in some embodiments, a user starts a mark model mode by contacting a stylus of the dental measurement device in a particular fashion e.g. tapping the device to a tooth surface a pre-determined number of times, e.g. contacting the device to a tooth surface at a higher pressure than that used for collecting measurements. For example, in some embodiments, a user starts a mark model mode by pressing on a button which is, for example, located on the dental measurement device e.g. located on a handle of the dental measurement device (e.g. handle 1544 FIG. 15A). Optionally, in some embodiments, starting a mark model mode, includes pressing a button (and/or inputting a command through another user interface) in addition to performing a command gesture before and/or after pressing the button (and/or inputting a command through another user interface).

At 1904, a portion of the dental measurement device (e.g. a stylus) is contacted to a mouth surface (e.g. a tooth surface) and a position of the contact point on the tooth surface (e.g. as measured by the dental measurement device) is marked on the 3D model. In some embodiments, a portion of the dental measurement device is contacted to a mouth surface and moved along the surface, and, in some embodiments, the model is marked with a contour of the contact movement.

In some embodiments, contact is (instead of between a portion of the dental measurement device) between another device and the mouth surface, where the dental measurement device (e.g. an intraoral scanner including one or more optical sensor) measures the contacted surface of the mouth surface. For example, in some embodiments, a pointer (e.g. unconnected to the dental measurement device) is used to mark the tooth model.

At 1906, in some embodiments, marking data is displayed on the tooth model and/or the marking data is saved in a memory, optionally with the mouth model.

FIG. 20 is a simplified schematic of marking of a tooth model, according to some embodiments of the disclosure. In some embodiments, a distal end 2040 of a dental measurement device is moved such that a stylus 2016 contacts a tooth surface and moves in contact with the tooth along a tooth surface contour 2090. In some embodiments, dental measurement device 2040 collects measurements of the position of a distal end of stylus 2016 during movement of the stylus along tooth surface contour 2090. In some embodiments, a display 2024 displays a tooth model 2026 which is a model of a portion of a mouth 2010. In some embodiments, the display displays by overlaying a measured tooth surface contour 2092 on tooth model 2026.

Exemplary Audio Feedback According to Some Embodiments

Figure 23:
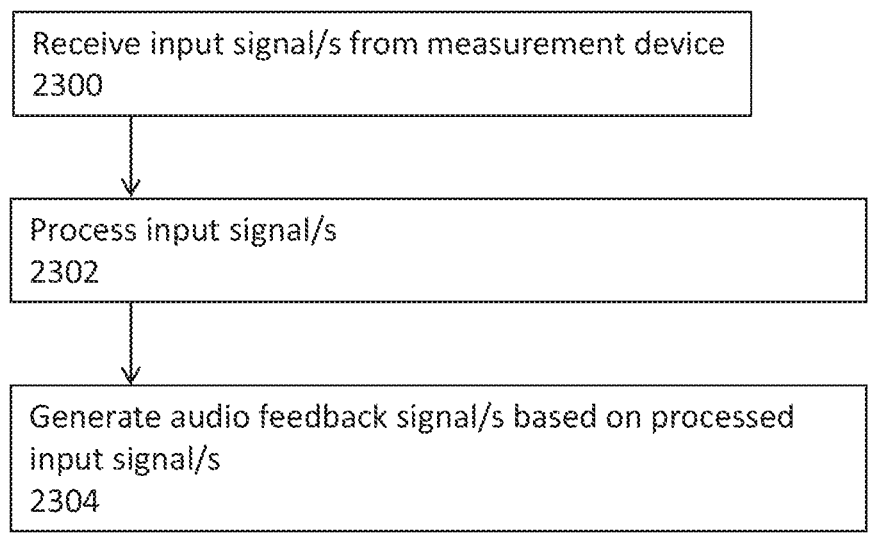
FIG. 23 is a flow chart of a method of audio feedback, according to some embodiments of the disclosure.

FIG. 23 is a flow chart of a method of audio display, according to some embodiments of the disclosure.

At 2300, in some embodiments, one or more input signal is received e.g. from a dental measurement device. For example, measurements from one or more sensor and/or one or more user input signal. For example, one or more input signal as described regarding step 1600, FIG. 16.

At 2302, in some embodiments, the input signal/s are processed, for example, by a processing application e.g. 506 FIG. 5. In some embodiments, input signal/s include measurements of a dental device stylus. For example, in some embodiments, one or more of; a size of a measurement device movement (e.g. of stylus movement), a rate of movement (e.g. of stylus movement), force of contact of the stylus (e.g. with another surface), texture of a surface over which the stylus is moved (e.g. tooth surface) whilst being in contact are identified from input signal/s.

At 2304, in some embodiments, based on processed input signal/s, audio feedback signal/s are generated. In some embodiments, audio feedback signals are broadcast to a user by one or more dental measurement device user interface, e.g. one or more speaker e.g. which is part of the dental measurement device.

In an exemplary embodiment, one or more parameter of an audio signal, for example, pitch and/or volume level, are adjusted, based on measured inputs from the stylus. In some embodiments, audio parameter/s are controlled by movement of the stylus, for example in response to large and/or high force movements of the stylus, in some embodiments, high pitch and/or volume audio signal/s are broadcast to a user.

In some embodiments, audio signals are generated and/or adjusted based on the different identified surfaces. In some embodiments, an audio feedback signal is selected and/or an existing signal is adjusted (e.g. volume and/or pitch and/or frequency of a repeated signal and/or melody) to indicate the region of the tooth that the stylus is in contact with.

In some embodiments, audio feedback signal/s are generated directly from stylus measurements. For example, in some embodiments, movement of a magnet coupled to the stylus and configured to move with the stylus is measured, the measurement being used to generate an audio signal e.g. the stylus operating as a patephone needle.

For example, in some embodiments, one or more magnet is connected to the dental measurement device stylus, movement of the stylus moving the magnet/s with respect to a stationary coil of the dental measurement device. Where, in some embodiments, the magnet and stylus move with respect to the stationary coil. In some embodiments, current generated at the coil by movement of the magnet provides a measurement signal regarding stylus movement. In some embodiments, this measurement signal is an input to an audio user interface. In some embodiments, the measurement signal is processed to generate an audio signal which, in some embodiments is broadcast to a user. Alternatively or additionally, in some embodiments, a coil connected to the stylus moves with respect to a stationary magnet of the dental measurement device to provide stylus movement measurements.

General

It is expected that during the life of a patent maturing from this application many relevant dental measurement technologies will be developed and the scope of the term dental measurement device is intended to include all such new technologies a priori.

As used herein:

the term "about" refers to +/−20%;

the terms "comprises", "comprising", "includes", "including", "having" and their conjugates mean "including but not limited to";

the term "consisting of" means "including and limited to"; and the term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this disclosure may be presented in a range format. It should be understood that the description in range format is merely for convenience and brevity and should not be construed as an inflexible limitation on the scope of the disclosure. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the disclosure, which are, for clarity, described in the context of separate embodiments, may also be provided in combination in a single embodiment. Conversely, various features of the disclosure, which are, for brevity, described in the context of a single embodiment, may also be provided separately or in any suitable sub-combination or as suitable in any other described embodiment of the disclosure. Certain features described in the context of various embodiments are not to be considered essential features of those embodiments, unless the embodiment is inoperative without those elements.

Although the disclosure has been described in conjunction with specific embodiments thereof, it is evident that many alternatives, modifications and variations will be apparent to those skilled in the art. Additionally, some embodiments of the present disclosure may be distinguishable from one and/or another teachings of the prior art by specifically lacking one and/or another feature/functionality—and thus claims directed to such embodiments include one and/or another negative limitations. Accordingly, the disclosure it is intended to embrace all alternatives, modifications, and variations that fall within the spirit and broad scope of claims that are supported by the current disclosure.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present disclosure. To the extent that section headings are used, they should not be construed as necessarily limiting.

What is claimed is:

1. A method for control of a dental measurement device comprising:
    measuring a gesture performed by moving a dental measurement device, the measuring said gesture comprising:
        using one or more sensors to produce a measurement signal;
        identifying a user command from the measurement signal;
        generating a control signal based on the identified user command; and
    modifying a function of one or more components of said dental measurement device based on the control signal, wherein:
        said gesture comprises contacting a portion of said dental measurement device to an object;
        said control signal based on said identified user command comprises selecting an area of said portion of said object being contacted by said dental measurement device; and
        said area being the area where said modifying said function will be applied.

2. The method of claim 1, wherein said gesture comprises one or more of:
    moving said dental measurement device;
    translating said dental measurement device in space;
    changing an orientation of said dental measurement device with respect to an object; and
    changing a proximity of said dental measurement device to an object.

3. The method of claim 1, wherein measuring the gesture comprises:
    measuring one or more of:
        movement of a stylus of a dental measurement device; and
        contact between said stylus and an object;
    and further comprising:
    controlling the device using said measuring.

4. The method of claim 1, wherein said object is a tooth and further comprising collecting a color measurement of said tooth.

5. The method of claim 4, wherein said collecting a color measurement of said tooth comprises collecting said color measurement at an area of said contacting to said tooth.

6. The method of claim 4, further comprising using a color reference on a stylus in order to identify a shade of said tooth.

7. The method of claim 3, wherein said movement of said stylus comprises one or more of:
    translations of said stylus in space;
    orientation of said stylus; and
    orientation of said dental measurement device with respect to a direction of gravity.

8. The method according to claim 1, wherein said measuring said gesture further comprises measuring using images collected by one or more imagers of said dental measurement device.

9. The method according to claim 1, further comprising providing information on a user interface comprised in said dental measurement device, wherein:
    said information includes feedback regarding measurements collected using said dental measurement device; and
    said feedback is audio feedback based on texture of a surface over which a stylus is moved.

10. The method of claim 1, further comprising providing haptic feedback regarding measurements collected using said dental measurement device.

11. The method of claim 1, further comprising providing feedback related to an angle between said dental measurement device and said dental object.

12. The method according to claim 1, further comprising:
    illuminating said object with structured light;
    collecting images of said illuminated object; and
    providing feedback indicating whether an angle between said dental measurement device and said object is above a threshold.

13. The method according to claim 2, wherein:
    said dental measurement device includes a stylus;
    said measuring further comprises contacting said stylus to said object; and
    further comprising providing feedback related to one or more of:
        an angle of said stylus with respect to said object; and
        a force of contact of said stylus with said object.

14. The method of claim 13, wherein said measuring further comprises measuring a distance between two points in a patient's mouth by touching the two points with a tip of said stylus.

15. The method of claim 13, wherein said measuring further comprises measuring said orientation of said dental measurement device with respect to a position of a user and identifying said position of said user with respect to said dental measurement device from images collected by an imager of said dental measurement device.

16. The method of claim 15, further comprising:
identifying said user's line of sight using one or more images of said user captured using one or more imagers of said dental measurement device;
identifying, from said image, a portion of said image obscured from a user's line of sight, wherein when displayed on a display, said portion aligns with a user view of patient mouth portions, and
displaying comprises displaying said portion of said image.

17. The method of claim 1, wherein:
at least a distal portion of said dental measurement device is inserted into a patient's mouth, and
said dental measurement device further comprises a display for displaying information associated with said measuring.

18. The method of claim 1, wherein said control signal controls an additional device inside the mouth.

19. The method of claim 1, further comprising displaying where measurement has been collected in relation to a tooth.

20. The method of claim 1 wherein:
said dental measurement device includes a plurality of user interfaces, and
said method further comprises selecting one or more user interface from said plurality of user interfaces based on said orientation.

* * * * *